(12) United States Patent
Jomaa et al.

(10) Patent No.: US 10,278,944 B1
(45) Date of Patent: May 7, 2019

(54) ANTICANCER ACTIVITY OF CIS-DIAMINE PLATINUM(II) COMPLEXES OF THIONES

(71) Applicant: KING FAHD UNIVERSITY OF PETROLEUM AND MINERALS, Dhahran (SA)

(72) Inventors: Mohammed Yagoub Jomaa, Dhahran (SA); Anvarhusein A. Isab, Dhahran (SA)

(73) Assignee: King Fahd University of Petroleum and Minerals, Dhahran (SA)

(*) Notice: Subject to any disclaimer, the term of this patent is extended or adjusted under 35 U.S.C. 154(b) by 0 days.

(21) Appl. No.: 15/794,384

(22) Filed: Oct. 26, 2017

(51) Int. Cl.
| | | |
|---|---|---|
| *A61K 31/22* | (2006.01) | |
| *A61K 31/095* | (2006.01) | |
| *A61K 31/505* | (2006.01) | |
| *A61K 31/282* | (2006.01) | |
| *A61K 33/24* | (2019.01) | |
| *C07F 15/00* | (2006.01) | |
| *A61K 31/551* | (2006.01) | |
| *A61K 31/4164* | (2006.01) | |

(52) U.S. Cl.
CPC .......... *A61K 31/282* (2013.01); *A61K 31/095* (2013.01); *A61K 31/505* (2013.01); *A61K 33/24* (2013.01); *C07F 15/0013* (2013.01); *A61K 31/4164* (2013.01); *A61K 31/551* (2013.01)

(58) Field of Classification Search
CPC .............. A61K 31/4164; A61K 31/505; A61K 31/551; A61K 31/22; A61K 31/095
USPC ......................................... 514/218, 269, 396
See application file for complete search history.

(56) References Cited

U.S. PATENT DOCUMENTS

2017/0073363 A1  3/2017  Altaf et al.

OTHER PUBLICATIONS

Seerat-Ur-Rehman, et al., "Synthesis, crystal structure and antimicrobial studies of a thione derivative of transplatin, trans-[Pt(NH3)2(Diaz)2]Cl2•2H2O (Diaz = 1,3-diazinane-2-thione)", Inorganic Chemistry Communications, vol. 36, pp. 68-71, (Aug. 29, 2013).

Mustafa, A.Z.A., et al., "Tetrakis(1-3-diazinane-2-thione)platinum(II) chloride monohydrate complex: Synthesis, spectroscopic characterization, crystal structure and in vitro cytotoxic activity against A549, MCF7, HCT15 and HeLa human cancer lines", Inorganic Chemistry Communications, vol. 44, pp. 159-163, (Mar. 27, 2014).

*Primary Examiner* — Raymond J Henley, III

(74) *Attorney, Agent, or Firm* — Oblon, McClelland, Maier & Neustadt, L.L.P.

(57) ABSTRACT

A method for treating a proliferative disease, disorder, or condition comprising administering a cis-diamine platinum (II) thione complex. A cis-diamine platinum(II) thione complex and compositions containing it.

20 Claims, 10 Drawing Sheets

Intra-strand crosslink

A549

A- 100µM  B- 50µM  C- 25µM  D- 12.5µM  E- Control

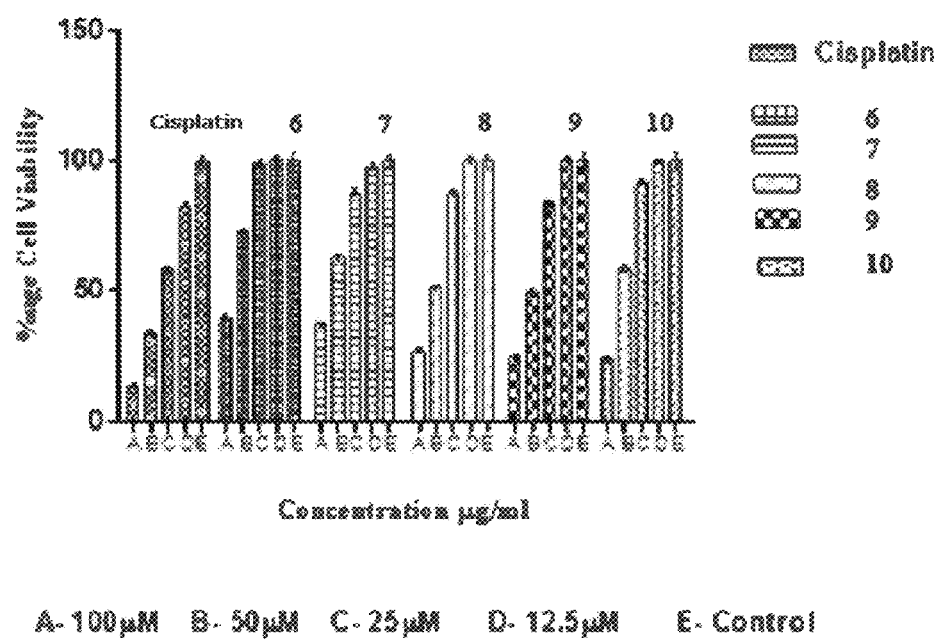

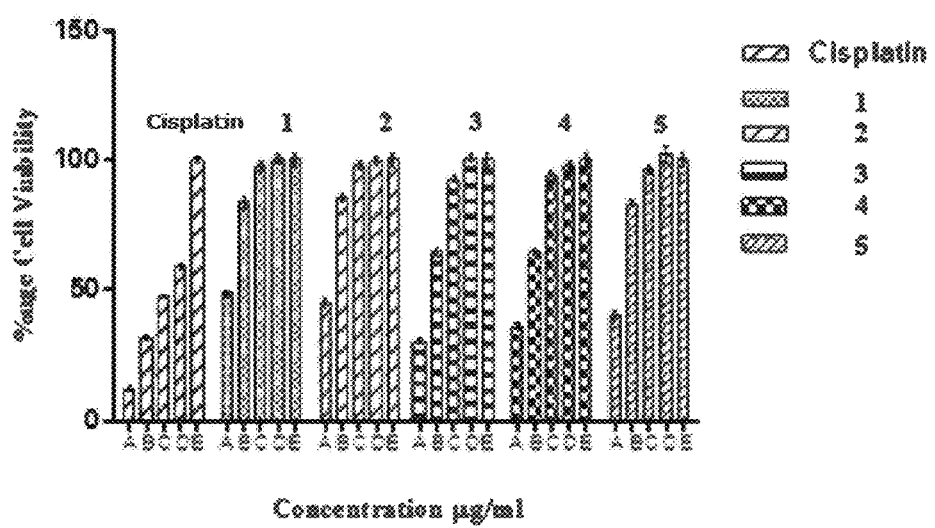

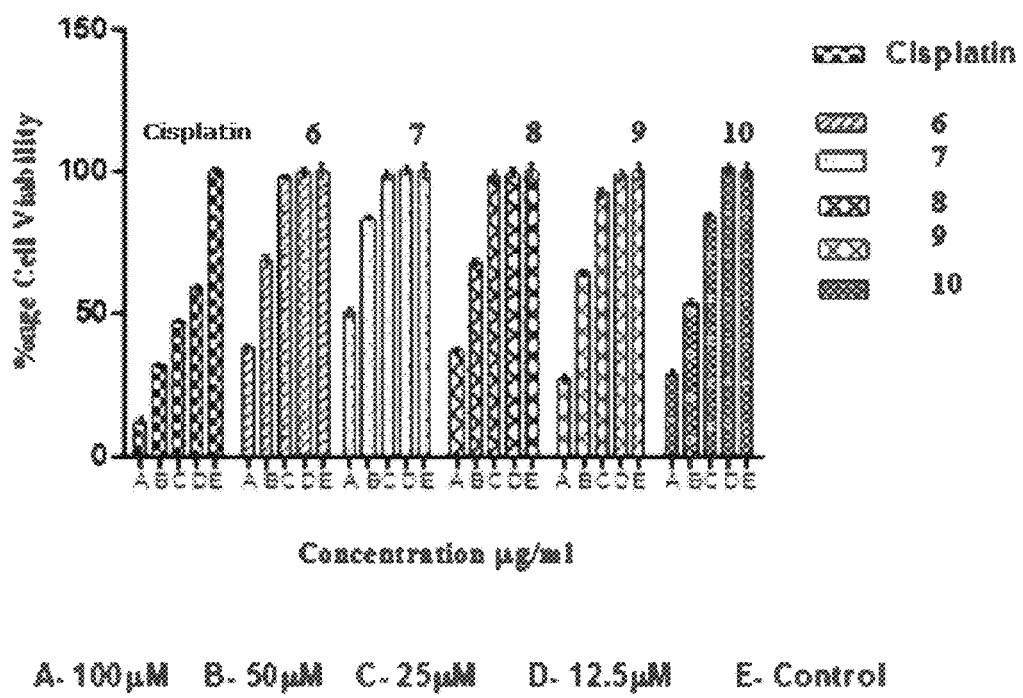

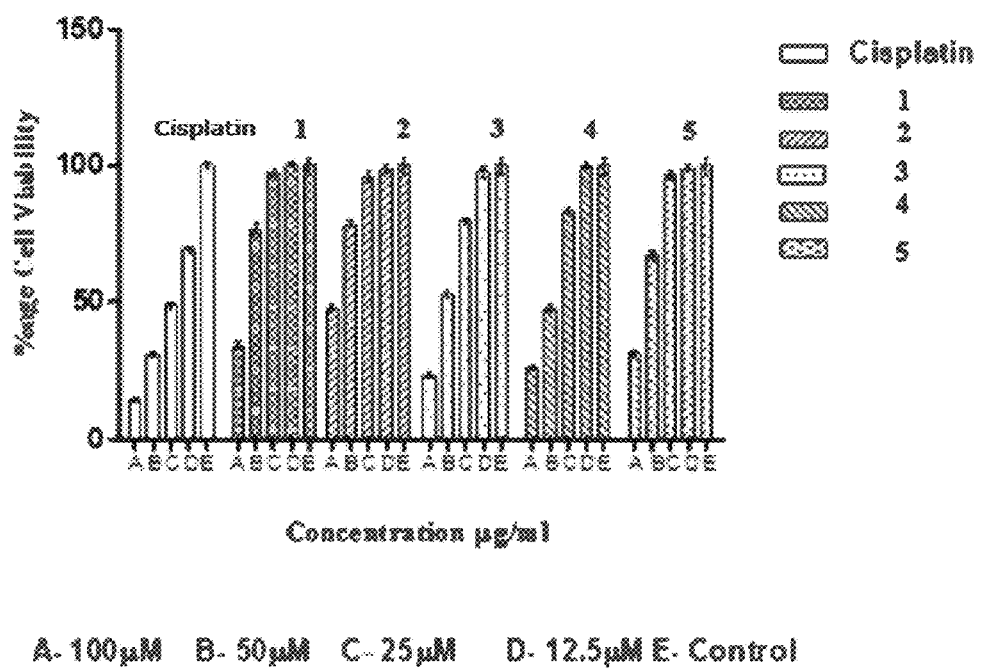

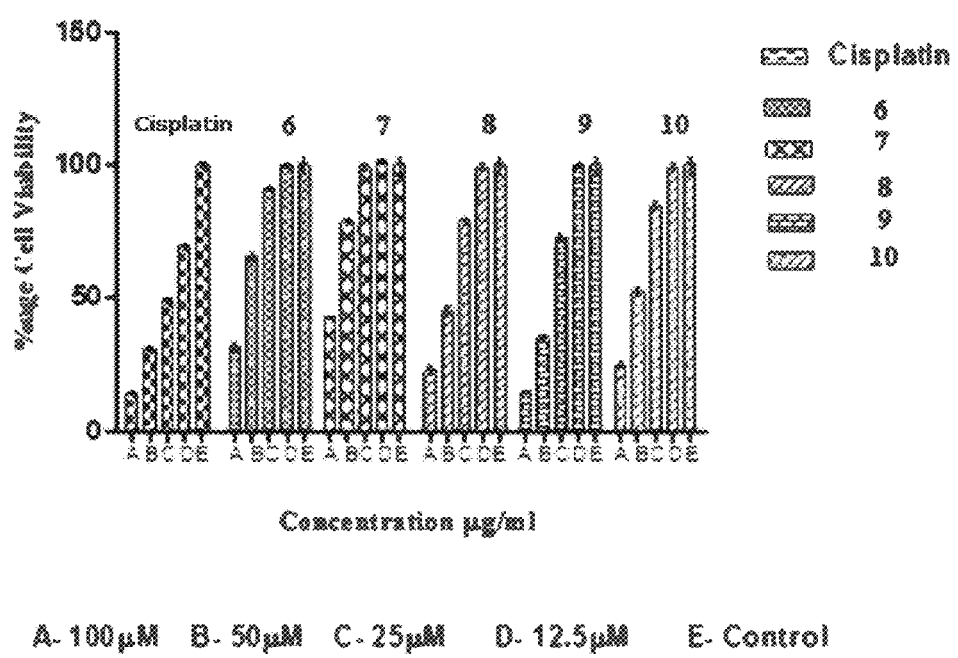

ANTICANCER ACTIVITY OF CIS-DIAMINE PLATINUM(II) COMPLEXES OF THIONES

BACKGROUND

Field of the Invention

The present disclosure relates to cis-amine Pt(II) thione complexes having the general formula, cis-[Pt(NH$_3$)$_2$(Thione)$_2$]2NO$_3$ and to a method for treating or inhibiting cancer using them.

Description of Related Art

The "background" description provided herein is for the purpose of generally presenting the context of the disclosure. Work of the presently named inventor(s), to the extent it is described in this background section, as well as aspects of the description which may not otherwise qualify as prior art at the time of filing, are neither expressly or impliedly admitted as prior art against the present invention.

Cisplatin is known to be one of the most effective drugs for the treatment of a variety of cancers. See T. C. Johnstone, K. Suntharalingam, S. J. Lippard, *Chem. Rev.* 116 (2016) 3436-3486; S. Dilruba, G. V. Kalayda, Cancer Chemotherapy and Pharmacology. 77 (2016) 1103-1124; N. J Wheate, S. Walker, G. E Craig, and R. Oun. Dalton Trans. 39 (2010) 8113-8127; J. J. Wilson, S. J. Lippard, Chem. Rev. 114 (2014) 4470-4495; Y. Jung, S. J. Lippard, Chem. Rev. 107 (2007) 1387-1407; D. Wong, S. J. Lippard, Nat. Rev. Drug Disc. 4 (2005) 307-320; K. S Lovejoy, S. J Lippard. Dalton Trans. (2009) 10651-10659; L. Kelland. Nat Rev Cancer. 7 (2007) 573-584; J. Reedijk, Eur. J. Inorg. Chem. (2009) 1303-1312; and S. Dasari, P. B. Tchounwou, Eur. J. Pharmacol. (2014) 364-378, each incorporated herein by reference in their entirety. However, the therapeutic use of cisplatin also leads to several side effects (e.g., nephrotoxicity and neurotoxicity) and drug resistance. See Dasair et al.; A. Florea and D. BUsselberg, Cancers (toxicity). 3 (2011) 1351-1371; J. T Hartmann and H. P. Lipp. Expert Opin. Pharmacother. 4 (2003) 889-901; V. M. Piccolini, M. G. Bottone, G. Bottiroli, S. A. De Pascali, F. P. Fanizzi, G. Bernocchi, Cell Biol Toxicol. 29 (2013) 339-353; L. Galluzzi, L. Senovilla, I. Vitale, J. Michels, I. Martins, O. Kepp, M. Castedo, G. Kroemer, Oncogene. 31 (2012) 1869-1883; D. J. Stewart, Crit. Rev. Oncol. Hematol. 63 (2007) 12-31; and J. Zisowsky, S. Koegel, S. Leyers, K. Devarakonda, M. U. Kassack, M. Osmak, U. Jaehde, Biochem. Pharmacol. 73 (2007) 298, each incorporated herein by reference in their entirety. Due to these limitations, efforts are continued to develop more effective drugs in order to reduce the toxicity of cisplatin and to overcome the cellular or inherent resistance. As a result, thousands of platinum compounds have been prepared and evaluated to check their anticancer effect. But, only a few of them have entered human clinical trials. See T. C. Johnstone et al.; S. Dilruba et al; N. J. Wheate et al.; J. J. Wilson et al; M. C. Ackley, C. G. Barry, A. M. Mounce, M. C. Farmer, B. E. Springer, C. S. Day, M. W. Wright, S. J. Berners-Price, S. M. Hess, U. Bierbach, J. Biol. Inorg. Chem. 9 (2004) 453; M. Galanski, M. A. Jakupec, B. K. Keppler, Curr. Med. Chem. 12 (2005) 2075-2094; E. Escribano, M. Font-Bardia, T. Calvet, J. Lorenzo, P. Gamez, V. Moreno, Inorg. Chim. Acta 394 (2013) 65-76; D Lebwohl, R. Canett. Eur. J. Cancer 34 (1998) 1522-1534; C. Gao, S. Gou, G. Xu, Chem. Pharm. Bull. 59 (2011) 851-854; B. A. Miles, A. E. Patterson, C. M. Vogels, A. Decken, J. C. Waller, P.-Jr. Morin, S. A. Westcott, Polyhedron 108 (2016) 23-29; G. Tamasi, M. Casolaro, A. Magnani, A. Sega, L. Chiasserini, L. Messori, C. Gabbiani, S. M Valiahdi, A. Michael, Jakupec, B. K. Keppler, B. Michael Hursthouse, R. Cini, J. Inorg. Biochem. 104 (2010) 799-814; R. Yin, S. Gou, X. Liu, L. Lou, J. Inorg. Biochem. 105 (2011) 1095-1101; W. Tian, L. He, Research on Chemical Intermediates. 41 (2015) 8725-8733; U. Kalinowska-Lis, J. Ochocki, K. Matlawska-Wasowska, Coord. Chem. Rev 252 (2008) 1328-1345; 1. Kostova, Recent Patents on Anti-Cancer Drug Discovery.1 (2006) 1-22; and M. Fanelli, M. Formica, V. Fusi, L. Giorgi, M. Micheloni, and P. Paoli, Coord. Chem Rev. 310 (2016) 41-79, each incorporated herein by reference in their entirety. Most of the clinically effective compounds have common structural unit (cis-PtN$_2$) as cisplatin. The biological activity associated with these compounds is normally associated with the presence of two fairly labile cis ligands, e.g., the two chlorido groups in cisplatin. See M. Fanelli et al.; E. R Jamieson, S. J Lippard. Chem Rev., 99 (1999) 2467-2498; and S. Ahmad, A. Isab, S. Ali, Transition Met. Chem. 31 (2006) 1003-1016, each incorporated herein by reference in their entirety. The Pt-DNA adducts produced by cisplatin and many of its analogues are almost identical, and would explain their similar patterns of tumor sensitivity and susceptibility to resistance. These adducts after cellular processing inhibit the normal transcription or replication of DNA and eventually lead to cell death. See T. C. Johnstone et al.; S. Dilruba et al; N. J. Wheate et al; J. J. Wilson et al.; Y. Jung et al.; D. Wong et al.; K. S. Lovejoy et al.; L. Kelland; J. Reedijk; S. Dasari et al.; E. R. Jamison et al.; S. Ahmad, A. Isab, S. Ali, Transition Met. Chem. 31 (2006) 1003-1016; S. Ahmad, Chem & Biodiver. 7 (2010) 543-566; S. G. Chaney, S. L. Campbell, E. Bassett, Y. Wu, Crit. Rev. Oncol. Hematol. 53 (2005) 3-11; S. V. Zutphen, J. Reedijk, Coord. Chem. Rev. 249 (2005) 2845-2853; S. Komeda. Metallomics, 3 (2011) 650-655; and J. Reedijk, Chem. Rev. 99 (1999) 2499, each incorporated herein by reference in their entirety.

Some platinum(II) complexes with sulfur-containing ligands such as dithiocarbamates, thiosemicarbazones and thioureas have shown superior or equal efficacy towards some human tumor cell lines and with less toxicity than cisplatin. See D. Fregona, L. Giovagnini, L. Ronconi, C. Marzano, A. Trevisan, S. Sitran, B. Biondi, F. Bordin, J. Inorg. Biochem. 93 (2003) 181-189; G. Faraglia, D. Fregona, S. Sitran, L. Giovagnini, C. Marzano, F. Baccichetti, U. Casellato, R. Graziania, J. Inorg. Biochem. 83 (2001) 31-40; L. Giovagnini, L. Ronconi, D. Aldinucci, D. Lorenzon, S. Sitran, D. Fregona. J. Med. Chem. 48 (2005) 1588; D. Kovala-Demertzi, P. N. Yadav, M. A. Demertzis, M. Coluccia. J. Inorg. Biochem. 78 (2000) 347; A. G. Quiroga, and C. N. Ranninger, Coord. Chem. Rev. 248 (2004) 119-133; D. Kovala-Demertzi, A. Papageorgiou, L. Papathanasis, A. Alexandratos, P. Dalezis, J. R. Miller, M. A. Demertzis, Eur. J. Med. Chem. 44 (2009) 1296-1302; G. Marverti, M. Cusumano, A. Ligabue, M. L. Di Pietro, P. A. Vainiglia, A. Ferrari, M. Bergomi, M. S. Moruzzi, C. Frassineti, J. Inorg. Biochem. 102 (2008) 699-712; L. Fuks, E. Anuszewska, H. Kruszewska, A. Krowczynski, J. Dudek, N. Sadlej-Sosnowska, Transition Met. Chem. 35 (2010) 639-647; A. Z. A. Mustafa, M. Altaf, M. Monim-ul-Mehboob, M. Fettouhi, M. 1. M Wazeer, A. A Isab, V. Dhuna, G. Bhatia, K. Dhuna, Inorg. Chem. Commun. 44 (2014) 159-163; and A. Zainelabdeen A. Mustafa, M. Monim-ul-Mehboob, M. Y. Jomaa, M. Altaf, M. Fettouhi, A. A. Isab, M. I. M. Wazeer, H. Stoeckli-Evans, G. Bhatia, V. Dhuna, J. Coord. Chem. 68 (2015) 3511-3524, each incorporated herein by reference in their entirety. Sulfur-containing molecules are also under study as chemoprotectants in platinum-based drugs chemotherapy. See S. Ahmad, A. Isab, S. Ali, Transition Met. Chem. 31 (2006) 1003-1016; and M. Galanski, each incorporated herein by reference in their entirety. These studies show that there is a significant potential in the studies of Pt(II) complexes of sulfur donor ligands such as thiones. Several thione derivatives of cisplatin displaying antitumor activities have also been reported. See G. Marverti, incorporated herein by reference in its entirety. To explore further about the antitumor potential of platinum-thione complexes, herein is disclosed the synthesis, spectroscopic characterization and anticancer activities of a number of cis-platinum (II) complexes with heterocyclic thiones ligand such as imidazolidine-2-thione (Imt), diazinane-2-thione (Diaz) and their derivatives as given in scheme 1.

The synthesis of these complexes and characterization by elemental analysis, IR and NMR ($^1$H & $^{13}$C) methods is one object of the present disclosure. It is a further object of the disclosure to compare spectroscopic data with the coordination of thiones to platinum(II) and show in vitro cytotoxic properties of all these complexes against three human cancer cell lines, which include; A549 (human lung carcinoma), MCF-7 (human breast carcinoma) and HTC15 (human colon cancer), in comparison to the therapeutically used anticancer agents cisplatin and carboplatin. The in vitro cytotoxicities in several cases are, comparable to cisplatin and higher than carboplatin.

BRIEF SUMMARY OF THE INVENTION

The following provides a summary of certain exemplary embodiments of the present invention. This summary is not an extensive overview and is not intended to identify key or critical aspects or elements of the present invention or to delineate its scope.

The invention is directed to platinum(II) complexes with thiones and to methods of treating cancer using these complexes. Several classes and ten complexes are exemplified; that is Complexes 1, 2, 3, 4, 5, 6, 7, 8, 9 and 10. The invention includes these complexes as well as their structural variants, for example, complexes containing substituted amines, substituted thiones, or those containing anions other than $NO_3$.

BRIEF DESCRIPTION OF THE DRAWINGS

The foregoing summary, as well as the following detailed description of preferred embodiments of the invention, will be better understood when read in conjunction with the appended drawings. It should be understood, however, that the invention is not limited to the precise features, arrangements, or instrumentalities shown.

FIGS. 4A and 4B. Activity of complexes (1)-(10) on A549 cells compared to Cisplatin. A549 is a human lung carcinoma cell line.

FIGS. 5A and 5B. Activity of complexes (1)-(10) on MCF7 cells compared to Cisplatin. MCF7 is a human breast carcinoma cell line.

FIGS. 6A and 6B. Activity of complexes (1)-(10) on HCT15 cells compared to Cisplatin.

DETAILED DESCRIPTION OF THE INVENTION

Figure 1:
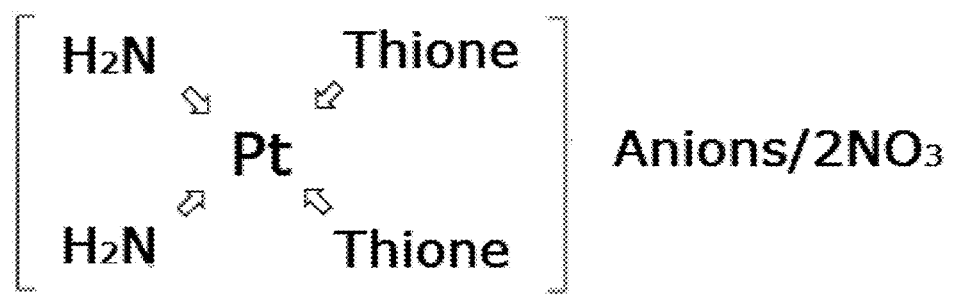
FIG. 1. General formula for cis-diamine Pt(II) thione complexes of the invention. In some embodiments, the $H_2N$ groups may be further substituted with non-hydrogen substituents.
Figure 2A:
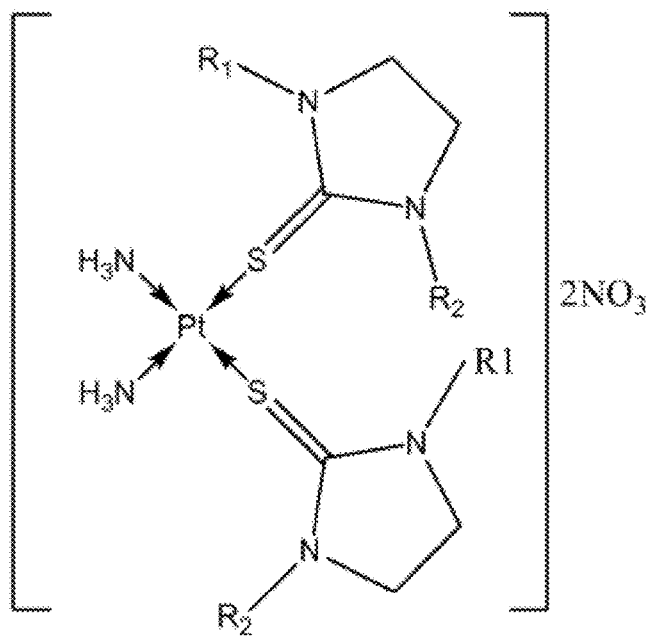
FIGS. 2A, 2B and 2C. Some examples of cis-diamine Pt(II) thione complexes. It can be clearly seen that form the structures the Pt(II) centre bounded to two amine ligands and two thione ligands via sulfur donor atoms in cis geometry. A trans geometry is the opposite with the same formula.
Figure 2B:
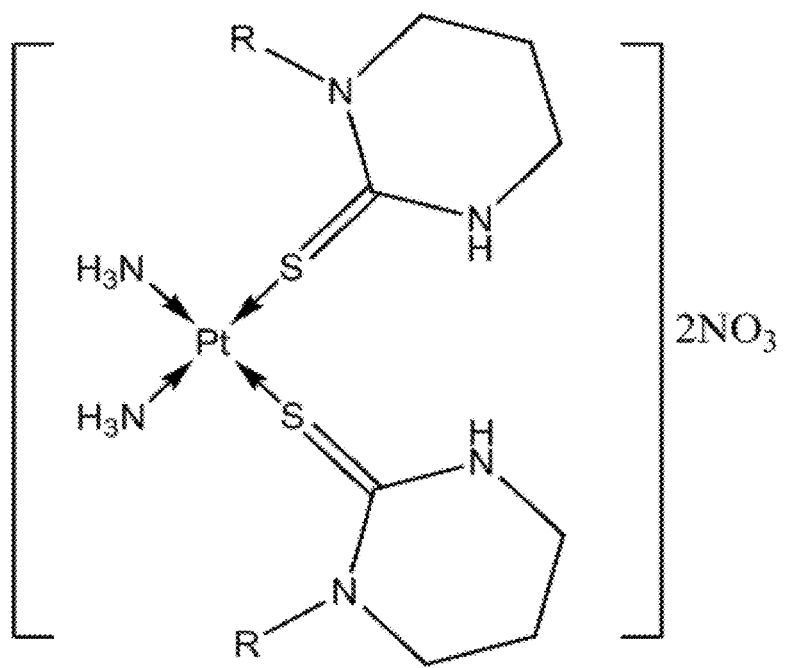
Figure 2C:
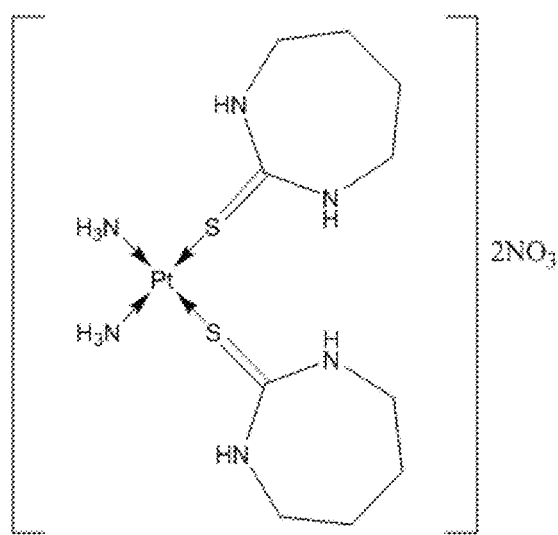

The invention is directed to cis-diamine platinum(II) thione complexes with thione ligands as shown by FIG. 1 or FIG. 2, including complexes (1), (2), (3), (4), (5), (6), (7), (8), (9) and (10), the core structures of these complexes, chemical variants of these core structures, and to methods that induce cytotoxicity in cancer or tumor cells.

The present disclosure will be better understood with reference to the following definitions:

As used herein "compound" and "complex" are used interchangeably and are intended to refer to a chemical entity, whether in a solid, liquid or gaseous phase and whether in a crude mixture or a purified and isolated form. For example, cis-diamino platinum(II) thione complex (1) of the invention may be referred to as 1, complex 1, or compound 1 and similarly with regard to other enumerated complexes disclosed herein.

Platinum(II) or Pt(II) describes platinum in an oxidation state of +2. One example of a platinum(II) compound is platinum chloride having the chemical formula $PtCl_2$.

Thiones include but are not limited to those described by the formulas below, wherein R is a suitable substituent that does not substantially eliminate the therapeutic properties of a cis-diamine Pt(II) thione complex produced with the substituted thione:

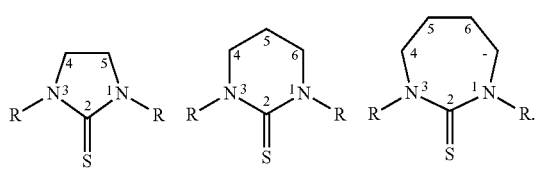

In some embodiments, the thiones may be further substituted on the carbons at ring positions 4, 5, 6, or 7 described in the rings above. Such substituents include those disclosed herein as other substituents.

Specific thiones exemplified herein include the following:

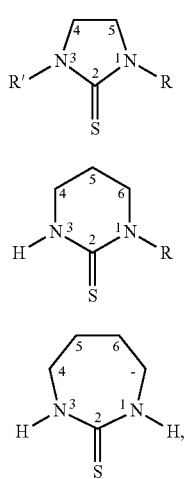

wherein thiones (a)-(j) are substituted as follows: (a) R=R'=H; Imidazolidine-2-thione (Imt), (b) R=H, R'=CH$_3$; N-methylimidazolidine-2-thione (MeImt), (c) R=CH$_3$, R' =CH$_3$; N,N'-dimethylimidazolidine-2-thione (Me$_2$Imt), (d) R=R' =C$_2$H$_5$; N,N-diethylimidazolidine-2-thione (Et$_2$Imt), (e) R=H, R'=C$_3$H$_7$; N-propylimidazolidine-2-thione (PrImt), (f) R=H, R'=i-C$_3$H$_7$; N-(isopropyl) imidazolidine-2-thione (iPrImt), (g) R=R'=i-C$_3$H$_7$; N,N'-(di-isopropyl)imidazolidine-2-thione (iPr$_2$Imt), (h) R=H; 1,3-Diazinane-2-thione (Diaz), (i) R=C$_2$H$_5$; N-ethyl-1,3-Diazinane-2-thione (EtDiaz), (j) 1,3-Diazepane-2-thione (Diap).

The terms "anion" or "counter-anion" refer to an anion, preferably a pharmaceutically acceptable anion that is associated with a positively charged platinum(II) complex core. Non-limiting examples of pharmaceutically acceptable counter-anions include nitrate, halides such as fluoride, chloride, bromide, iodide; sulfate; phosphate; amide; methanesulfonate; ethanesulfonate; p-toluenesulfonate, salicylate, malate, maleate, succinate, tartrate; citrate; acetate; perchlorate; trifluoromethanesulfonate (triflate); acetylacetonate; hexafluorophosphate; and hexafluoroacetylacetonate.

Amines.

The amine components of the complex, independently, have the formula NR1R2, where R1 and R2 may both be hydrogen, one of R1 or R2 may be hydrogen, or neither R1 or R2 is hydrogen. Non-hydrogen substituents include alkyl, such as C1-C6 alkyl or aryl either of which may be further substituted. Other substituents disclosed herein may also be used provided they do not negate the cytotoxic activity of a platinum(II) complex.

Variants.

Structurally-related variants of the complexes exemplified herein include cis-diamine Pt(II) complexes where at least one of R1 and R2 on the amine group has a non-hydrogen substituent, such as alkyl (e.g., C$_1$-C$_6$ alkyl) or aryl; complexes where the thione component is substituted, and/or complexes wherein the one or both NO$_3$ anions are replaced with another anion. Heterocyclic thiones are stable ligands and can be substituted often without substantial effects on a cis-diamine Pt(II) thione complex's therapeutic, cytotoxic or anti-cancer properties.

Other substituents that may appear on the amine (i.e., as R$_1$ and/or R$_2$) and thione components of the Pt(II) complex include but are not limited those defined below.

Alkyl, as used herein, which unless otherwise specified, refers to a straight or branched hydrocarbon fragment such as a C$_1$-C$_6$ group. Non-limiting examples of such hydrocarbon fragments include methyl, ethyl, propyl, isopropyl, butyl, isobutyl, t-butyl, pentyl, isopentyl, neopentyl, hexyl, isohexyl, 3-methylpentyl, 2,2-dimethylbutyl, and 2,3-dimethylbutyl. As used herein, the term "cycloalkyl" refers to a cyclized alkyl group. Exemplary cycloalkyl groups include, but are not limited to, cyclopropyl, cyclobutyl, cyclopentyl, cyclohexyl, norbornyl, and adamantyl. Branched cycloalkyl groups, for example, I-methylcyclopropyl and 2-methycyclopropyl groups, are included in the definition of cycloalkyl as used in the present disclosure. The term "alkenyl" refers to a straight, branched, or cyclic hydrocarbon fragment containing at least one C=C double bond. Exemplary alkenyl groups include, without limitation, 1-propenyl, 2-propenyl (or "allyl"), 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, I-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, and 9-decenyl. The term "aryl", as used herein, and unless otherwise specified, refers to phenyl, biphenyl, naphthyl, anthracenyl, and the like. The term "heteroaryl" refers to an aryl group where at least one carbon atom is replaced with a heteroatom (e.g. nitrogen, oxygen, sulfur) and can be indolyl, furyl, imidazolyl, triazolyl, triazinyl, oxazolyl, isoxazolyl, thiazolyl, isothiazolyl, pyrazolyl, pyrrolyl, pyrazinyl, tetrazolyl, pyridyl (or its N-oxide), thienyl, pyrimidinyl (or its N-oxide), IH-indolyl, isoquinolyl (or its N-oxide), or quinolyl (or its N-oxide), for example. As used herein, the term "substituted" refers to at least one hydrogen atom that is replaced with a non-hydrogen group, provided that normal valencies are maintained and that the substitution results in a stable compound. When a compound or a R group is noted as "optionally substituted", the substituents are selected from the exemplary group including, but not limited to, aroyl (as defined hereinafter); halogen (e.g. chlorine, bromine, fluorine or iodine); alkoxy (i.e. straight or branched chain alkoxy having 1 to 10 carbon atoms, and includes, for example, methoxy, ethoxy, propoxy, isopropoxy, butoxy, isobutoxy, sec-butoxy, tert-butoxy, pentoxy, isopentoxy, hexyloxy, heptyloxy, octyloxy, nonyloxy, and decyloxy); cycloalkyloxy including cyclopentyloxy, cyclohexyloxy, and cycloheptyloxy; aryloxy including phenoxy and phenoxy substituted with halogen, alkyl, alkoxy, and haloalkyl (which refers to straight or branched chain alkyl having 1 to 8 carbon atoms which are substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-tri-fluoroethyl, 2,3,3-trifluoropropyl, 1,1,2,2-tetrafluoroethyl, 2,2,3,3-tetrafluoropropyl); hydrocarbyl; arylalkyl; hydroxy; alkoxy; oxo; alkanoyl; alkanoyloxy; amino; alkylamino; arylamino; arylalkylamino; disubstituted amines (e.g., in which the two amino substituents are selected from a group including, but not limited to, alkyl, aryl, or arylalkyl); alkanoylamino; thiol; alkylthio; arylthio; arylalkylthio; alkylthiono; arylthiono; aryalkylthiono; alkylsulfonyl; arylsulfonyl; aryalkylsulfonyl; sulfonamido (e.g., —SO$_2$NH$_2$); substituted sulfonamide; nitro; cyano; carboxy; carbamyl (e.g., —CONH$_2$, —CONHalkyl, —CONHaryl, —CONHarylalkyl or cases where there are two substituents on one nitrogen from alkyl, aryl, or arylalkyl); alkoxycarbonyl; aryl; heteroarylcarbonyl; heterocyclyl; and mixtures thereof and the like. The substituents may be either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety). The term "heterocyclyl" as used in this disclosure refers to a 3-8, preferably 4-8, more preferably 4-7 membered monocyclic ring or a fused 8-12 membered bicyclic ring which may be saturated or partially unsaturated, which monocyclic or bicyclic ring contains 1 to 4 heteroatoms selected from oxygen, nitrogen, silicon, or sulfur. Examples of such monocyclic rings include oxaziridinyl, homopiperazinyl, oxiranyl, dioxiranyl, aziridinyl, pyrrolidinyl, azetidinyl, pyrazolidinyl, oxazolidinyl, piperidinyl, piperazinyl, morpholinyl, thiomorpholinyl, thiazolidinyl, hydantoinyl, valerolactamyl, oxiranyl, oxetanyl, dioxolanyl, dioxanyl, oxathiolanyl, oxathianyl, dithianyl, dihydrofuranyl, tetrahydrofuranyl, dihydropyranyl, tetrahydropyranyl, tetrahydropyridyl, tetrahydropyrimidinyl, tetrahydrothiophenyl, tetrahydrothiopyranyl, diazepanyl, and azepanyl. Examples of such bicyclic rings include indolinyl, isoindolinyl, benzopyranyl, quinuclidinyl, 2,3,4,5-tetrahydro-1,3,benzazepine, 4-(benzo-1,3,dioxol-5-methyl)piperazine, and tetrahydroisoquinolinyl. Further, "substituted heterocyclyl" may refer to a heterocyclyl ring which has additional (e.g. one or more) oxygen atoms bonded to the ring atoms of parent heterocylcyl ring. An example of a heterocyclyl substituted with one or more oxygen atoms is 1,1-dioxido-1,3-thiazolidinyl. The term "alkylthio" as used in this disclosure refers to a divalent sulfur with alkyl occupying one of the valencies and includes the groups methylthio, ethylthio, propylthio, butylthio, pentylthio, hexylthio, and octylthio. The term "alkanoyl" as used in this disclosure refers to an alkyl group having 2 to 18 carbon atoms that is bound with a double bond to an oxygen atom. Examples of alkanoyl include, acetyl, propionyl, butyryl, isobutyryl, pivaloyl, valeryl, hexanoyl, octanoyl, lauroyl, and stearoyl. Examples of aroyl are benzoyl and naphthoyl, and "substituted aroyl" may refer to benzoyl or naphthoyl substituted by at least one substituent including those selected from halogen, amino, nitro, hydroxy, alkyl, alkoxy and haloalkyl on the benzene or naphthalene ring. The term "arylalkyl" as used in this disclosure refers to a straight or branched chain alkyl moiety having 1 to 8 carbon atoms that is substituted by an aryl group or a substituted aryl group having 6 to 12 carbon atoms, and includes benzyl, 2-phenethyl, 2-methylbenzyl, 3-methylbenzyl, 4-methylbenzyl, 2,4-dimethylbenzyl, 2-(4-ethylphenyl)ethyl, 3-(3-propylphenyl)propyl. The term "heteroarylcarbonyl" as used in this disclosure refers to a heteroaryl moiety with 5 to 10 membered mono- or fused-heteroaromatic ring having at least one heteroatom selected from nitrogen, oxygen and sulfur as mentioned above, and includes, for example, furoyl, nicotinoyl, isonicotinoyl, pyrazolylcarbonyl, imidazolylcarbonyl, pyrimidinylcarbonyl, and benzimidazolyl-carbonyl. Further, "substituted heteroarylcarbonyl" may refer to the above mentioned heteroarylcarbonyl which is substituted by at least one substituent selected from halogen, amino, vitro, hydroxy, alkoxy and haloalkyl on the heteroaryl nucleus, and includes, for example, 2-oxo-1,3-dioxolan-4-ylmethyl, 2-oxo-1,3-dioxan-5-yl. "Vinyl" refers to an unsaturated substituent having at least one unsaturated double bond and having the formula CH2═CH—. Accordingly, said "substituted vinyl" may refer to the above vinyl substituent having at least one of the protons on the terminal carbon atom replaced with alkyl, cycloalkyl, cycloalkylalkyl, aryl, substituted aryl, heteroaryl or substituted heteroaryl. The term "hydrocarbyl" as used herein refers to a univalent hydrocarbon group containing up to about 24 carbon atoms (i.e. a group containing only carbon and hydrogen atoms) and that is devoid of olefinic and acetylenic unsaturation, and includes alkyl, cycloalkyl, alkyl-substituted cycloalkyl, cycloalkyl-substituted cycloalkyl, cycloalkylalkyl, aryl, alkyl-substituted aryl, cycloalkyl-substituted aryl, arylalkyl, alkyl-substituted aralkyl, and cycloalkyl-substituted aralkyl. Further, functionally-substituted hydrocarbyl groups may refer to a hydrocarbyl group that is substituted by one or more functional groups selected from halogen atoms, amino, nitro, hydroxy, hydrocarbyloxy (including alkoxy, cycloalkyloxy, and aryloxy), hydrocarbylthio (including alkylthio, cycloalkylthio, and arylthio), heteroaryl, substituted heteroaryl, alkanoyl, aroyl, substituted aroyl, heteroarylcarbonyl, and substituted heteroarylcarbonyl. In some embodiments, hydrogen is replaced by C1-C6 alkyl on atoms not participating in the Pt(II)-S bond. The hydrophobicity or hydrophilicity of the complex may be adjusted by selecting appropriate substituents for the thione component of the complex or by selection of different counteranions or complexing components. A size and relative degree of hydrophilicity or hydrophobicity suitable for a particular mode of administration and uptake of the complex at a desired site of action. For example, a complex may be made more hydrophobic by substitution of the thione moiety with alkyl or aryl to increase its ability to cross a lipid bilayer or to interact with non-polar compounds. Alternatively it may be made more hydrophilic by substitution of the thione moiety with a more polar substituent to facilitate serum binding, adsorption into water-containing bodily fluids, or interaction with polar compounds.

Compositions.

In many embodiments, the cis-diamine platinum(II) complexes of the invention, the salt thereof, the solvate thereof, a prodrug thereof, or a combination thereof is formulated as a pharmaceutically acceptable composition. As used herein, a "composition" refers to a mixture of the active ingredient with at least one other chemical component, such as a pharmaceutically acceptable carrier or excipient. One purpose of a composition is to facilitate administration of the cis-diamine platinum(II) thione complex of the invention, the salt thereof, the solvate thereof, the prodrug thereof, or a combination thereof to a subject. Depending on the intended mode of administration (oral, parenteral, or topical), the composition can be in the form of solid, semi-solid, liquid, or aerosol dosage forms, such as tablets, suppositories, pills, capsules, powders, liquids, or suspensions, preferably in unit dosage form suitable for single administration of a precise dosage. The phrase "pharmaceutically acceptable" as used herein refers to compounds, counterions, materials, compositions, and/or dosage forms which are, within the scope of sound medical judgment, suitable for use in contact with the tissues of human beings and animals without excessive toxicity, irritation, allergic response, or other problem or complication and commensurate with a reasonable benefit/risk ratio. Therefore, the composition refers to the combination of an active ingredient with a carrier or excipient, inert or active, making the composition especially suitable for diagnostic or therapeutic use in vivo, ex vivo, or in vitro.

As used herein, a pharmaceutically acceptable carrier refers to a carrier or diluent that does not cause significant irritation to an organism, does not abrogate the biological activity and properties of the administered active ingredient, and/or does not interact in a deleterious manner with the other components of the composition in which it is contained. The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005, which is incorporated herein by reference in its entirety. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS® (BASF; Florham Park, N.J.). An "excipient" refers to an inert substance added to a composition to further facilitate administration of a compound. Examples, without limitation, of excipients include calcium carbonate, calcium phosphate, various sugars and types of starch, cellulose derivatives, gelatin, vegetable oils, and polyethylene glycols.

In other embodiments, the composition has various release rates (e.g. controlled release or immediate release). Immediate release refers to the release of an active ingredient substantially immediately upon administration. In another embodiment, immediate release occurs when there is dissolution of an active ingredient within 1-20 minutes after administration. Dissolution can be of all or less than all (e.g., about 70%, about 75%, about 80%, about 85%, about 90%, about 91%, about 92%, about 93%, about 94%, about 95%, about 96%, about 97%, about 98%, about 99%, about 99.5%, 99.9%, or 99.99%) of the active ingredient. In another embodiment, immediate release results in complete or less than complete dissolution within about 1 hour following administration. Dissolution can be in a subject's stomach and/or intestine. In one embodiment, immediate release results in dissolution of an active ingredient within 1-20 minutes after entering the stomach. For example, dissolution of 100% of an active ingredient can occur in the prescribed time. In another embodiment, immediate release results in complete or less than complete dissolution within about 1 hour following rectal administration. In some embodiments, immediate release is through inhalation, such that dissolution occurs in a subject's lungs.

Controlled-release or sustained-release refers to the release of an active ingredient from a composition or dosage form in which the active ingredient is released over an extended period of time. In one embodiment, controlled-release results in dissolution of an active ingredient within 20-180 minutes after entering the stomach. In another embodiment, controlled-release occurs when there is dissolution of an active ingredient within 20-180 minutes after being swallowed. In another embodiment, controlled-release occurs when there is dissolution of an active ingredient within 20-180 minutes after entering the intestine. In another embodiment, controlled-release results in substantially complete dissolution after at least 1 hour following administration. In another embodiment, controlled-release results in substantially complete dissolution after at least 1 hour following oral administration. In another embodiment, controlled-release results in substantially complete dissolution after at least 1 hour following rectal administration. In another embodiment, controlled-release results in substantially complete release of the active component after or over at least 1, 2, 4, 8, 12, 24 hours or 2, 3, 4, 5, 6, or 7 days (or any intermediate value within this range) following administration including a depot administration into or around a tumor. In one embodiment, the composition is not a controlled-release composition.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavoring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids, such as oleic acid, find use in the preparation of injectables. Dimethyl acetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug.

Topical administration can also involve the use of transdermal administration such as transdermal patches or iontophoresis devices. Formulation of drugs is discussed in, for example, Hoover, John E., Remington's Pharmaceutical Sciences, Mack Publishing Co., Easton, Pa., 1975. Another example of includes Liberman, H. A. and Lachman, L., Eds., Pharmaceutical Dosage Forms, Marcel Decker, New York, N.Y., 1980, which is incorporated herein by reference in its entirety).

Other Active Ingredients.

In some embodiments, other active ingredients in addition to the cis-diamine platinum(II) thione complex may be incorporated into a composition or separately administered in conjunction with a cis-diamine platinum(II) thione complex. In one embodiment, the composition is used for treating cancer and further comprises a second active ingredient, such as a chemotherapeutic or immunotherapeutic agent, for the treatment or prevention of neoplasm, of tumor or cancer cell division, growth, proliferation and/or metastasis in the subject; induction of death or apoptosis of tumor and/or cancer cells; and/or any other form of proliferative disorder. Exemplary chemotherapeutic agents include, without limitation, aflibercept, asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosfamide, irinotecan, lomustine, mechlorethamine, melphalan, mercaptopurine, methotrexate, mitomycin, mitoxantrone, pentostatin, procarbazine, topotecan, vinblastine, vincristine, retinoic acid, oxaliplatin, carboplatin, 5-fluorouracil, teniposide, amasacrine, docetaxel, paclitaxel, vinorelbine, bortezomib, clofarabine, capecitabine, actinomycin D, epirubicin, vindesine, methotrexate, 6-thioguanine, tipifarnib, imatinib, erlotinib, sorafenib, sunitinib, dasatinib, nilotinib, lapatinib, gefitinib, temsirolimus, everolimus, rapamycin, bosutinib, pzopanib, axitinib, neratinib, vatalanib, pazopanib, midostaurin, enzastaurin, trastuzumab, cetuximab, panitumumab, rituximab, bevacizumab, mapatumumab, conatumumab, and lexatumumab. The composition may comprise 0.1-50 wt % of the second active ingredient, preferably 10-40 wt %, more preferably 10-20 wt %, relative to the weight of the first active ingredient.

Subjects.

The terms "patient", "subject", and "individual" are used interchangeably. As used herein, they refer to individuals suffering from a disease, at risk of further progression of a disease, or at risk of acquiring or developing the disease. None of these terms require that the individual be under the care and/or supervision of a medical professional.

These terms generally refer to humans, but also apply to mammals, avians and other animals, especially domesticated or ecologically or commercially valuable animals. Mammals include non-human primates, such as chimpanzees, and other apes and monkey species, farm animals, such as cattle, horses, sheep, goats, swine, domestic animals, such as rabbits, dogs, and cats, laboratory animals including rodents, such as rats, mice and guinea pigs, and the like. In a preferred embodiment, the subject is a human.

A subject in need of treatment includes a subject already with a disease such as cancer, a subject who does not yet experience or exhibit symptoms of the disease, and a subject who is predisposed to the disease for example based on family history or genetic profile. In preferred embodiments, the subject is a person who is predisposed to cancer such as a person with a family history of cancer. In another embodiment, the subject refers to a cancer patient who has been previously administered/treated with cisplatin and have cisplatin resistance, for example in the form of high ERCC1 mRNA levels, overexpression of HER-2/neu, activation of the PI3-K/Akt pathway, loss of p53 function, and/or overexpression of antiapoptotic bcl-2).

The term active ingredient, as used herein, refers to an ingredient in the composition that is biologically active, for example, the cis-diamine platinum(II) complexes disclosed herein, a salt thereof, a prodrug thereof, or a solvate thereof. Other active ingredients include, but are not limited to, those that exert a substantial pharmacokinetic or pharmacodynamic activity when in admixture with a cis-diamine platinum(II) thione complex, for example, other anti-cancer drugs, immunopotentiators, or other agents.

Antitumor properties may be evaluated by methods known in the art, including these described by and incorporated by reference to Y. F. To, R. W.-Y. Sun, Y. Chen, V. S.-F. Chan, W.-Y. Yu, P. K.-H. Tam, C.-M. Che and C.-L. S. Lin, Int. J. Cancer, 2009, 124, 1971-1979; C. T. Lum, Z. F. Yang, H. Y. Li, R. W.-Y. Sun, S. T. Fan, R. T. P. Poon, M. C. M. Lin, C.-M. Che and H. F. Kung, Int. J. Cancer, 2006, 118, 1527-1538; C. T. Lum, A. S.-T. Wong, M. C. M. Lin, C.-M. Che and R. W.-Y. Sun, Chem. Commun., 2013, 49, 4364-4366; C.-M. Che, R. W.-Y. Sun, W.-Y. Yu, C.-B. Ko, N. Zhu and H. Sun, Chem. Commun., 2003, 1718-1719; Y. Wang, Q.-Y. He, R. W.-Y. Sun, C.-M. Che and J.-F. Chiu, Eur. J. Pharmacol., 2007, 554, 113-122—each incorporated by reference.

Cytotoxic Activity.

In one embodiment, the $IC_{50}$ of the platinum(II) complexes is in a range of 0.01-200 µM, 0.1-100 µM, 1-100 µM, 10-90 µM, 20-80 µM, 30-80 µM, 40-80 µM, 50-80 µM, or 50-75 µM. These ranges include all intermediate subranges and values. As used herein, the term "$IC_{50}$" refers to a concentration of a platinum(II) complex, the salt thereof, the prodrug thereof, or the solvate thereof, which causes the death of 50% of cancer or proliferating cells in 72 hours (3 days) such as the A549 (human lung carcinoma), MCF-7 (human breast carcinoma) and HTC15 (human colon cancer) cell lines described herein. The $IC_{50}$ can be determined by standard cell viability assays, such as, without limitation, ATP test, calcein AM assay, clonogenic assay, ethidium homodimer assay, Evans blue assay, Fluorescein diacetate hydrolysis/propidium iodide staining assay, flow cytometry assay, formazan-based assays (MTT, XTT), green fluorescent protein assay, lactate dehydrogenase assay, methyl violet assay, propidium iodide assay, Resazurin assay, Trypan Blue assay and TUNEL assay. Preferably, a MTT assay and/or a Trypan Blue assay is used.

Figure 3A:
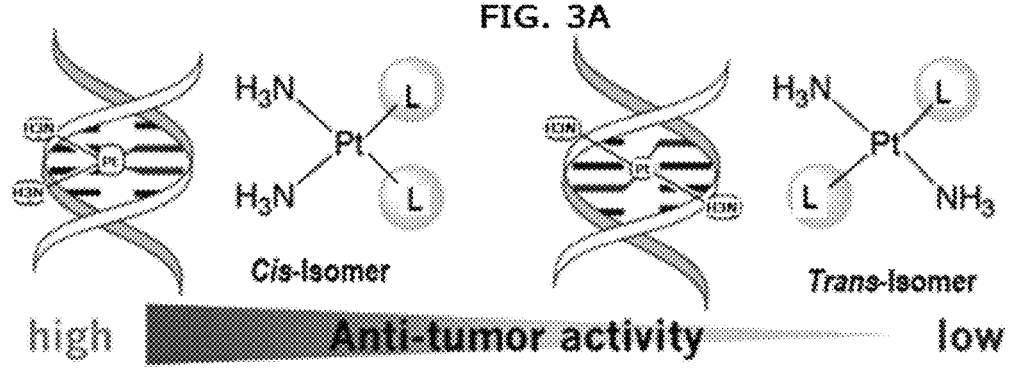
FIG. 3A. Comparison of antitumor activity and DNA binding of cis-diamine complexes and trans-diamine complexes. The Pt(II) complexes of the invention are cis-isomers which contribute to their biological anticancer activity. Complexes having a trans geometry, such as trans-platins, have been found to be less active. Cis- and trans compounds bind to DNA in different ways and produce different biological effects.
Figure 3B:
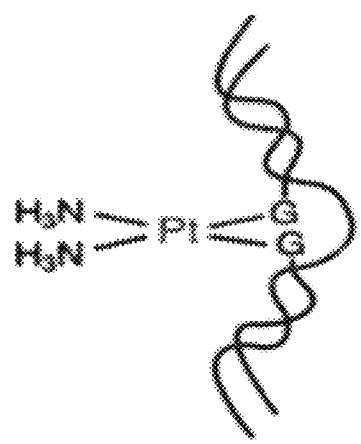
FIG. 3B depicts intra-strand crosslink via cis-diamine Pt(II) complex. Platination can form different DNA adducts. It was found that 60-65% of the formed adducts are 1, 2-d(GpG) intrastrand cross-links binding with two neighbouring guanine in the same strand, which can be achieved only through cis configuration
Figure 3C:
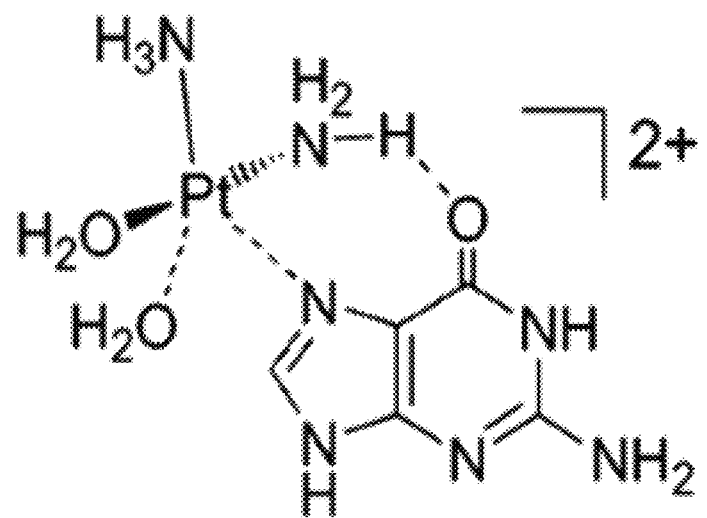
FIG. 3C depicts interaction of a Pt(II) complex with guanine.

While not being bound to any particular explanation, it is believed that interaction of the complexes of the invention with polynucleotides account for cytotoxic activity. As shown by FIG. 3C, the N7 atoms of the imidazole rings in the DNA purine bases guanine and adenine are most nucleophic and accessible site which can be a major target for platination. After the binding of platinum to the nucleophilic site N7 of guanine and adenine, the amine ligands act as hydrogen-bond donors, whereas C6 position in the guanine ring (oxo group) and (amino group) in the case of adenine ring, known to be hydrogen-bond acceptors. This hydrogen bond, especially between the N—H . . . O=C6 in case of guanine, is a factor in the stabilization of the Pt-DNA adduct. Moreover, it is believed that the N7 atoms of the imidazole rings in the DNA purine bases guanine and adenine is most nucleophic and accessible site which can be a major target for platination. After the binding of platinum to the nucleophilic site N7 of guanine and adenine, the amine ligands act as hydrogen-bond donors, whereas C6 position in the guanine ring (oxo group) and (amino group) in case of adenine ring, known to be hydrogen-bond acceptors. This hydrogen bond especially between the N—H . . . O=C6 in case of guanine is a factor in the stabilization of the Pt-DNA adduct.[

Nephrotoxicity.

Cisplatin is known to be nephrotoxic. Nephrotoxicity of cisplatin or other anticancer drugs may be evaluated by comparison with the Pt(II) thione complexes of the invention by known methods such as evaluation of nephrotoxicity through blood tests including a measurement of blood urea nitrogen (BUN), concentration of serum creatinine, glomerular filtration rate and/or creatinine clearance. Other methods may also be used to assess absolute or relative nephrotoxicity such as those described by Kim, et al., *Drug-Induced Nephrotoxicity and Its Biomarkers*, Biomol Ther (Seoul). 2012 May; 20(3): 268-272, see the text at www.ncbi.nlm.nih.gov/pmc/articles/PMC3794522/ (last accessed Oct. 19, 2017, incorporated by reference). In some embodiments, a cis-diamine Pt(II) thione complex of the invention will not exhibit substantial nephrotoxicity or will exhibit 10, 20, 30, 40, 50, 60, 70, 80, 90, or 95% of the nephrotoxicity of cisplatin or other anticancer drug based on equivalent dosage or on equivalent effective dosages.

Neurotoxicity.

Neurotoxicity is toxicity in the nervous system. It occurs when exposure to natural or artificial toxic substances, which are called neurotoxins, alters the normal activity of the nervous system in such a way as to cause damage to nervous tissue. This can eventually disrupt or even kill neurons, key cells that transmit and process signals in the brain and other parts of the nervous system. Neurotoxicity can result from exposure to substances used in chemotherapy, radiation treatment, drug therapies, certain drug abuse, and organ transplants, as well as exposure to heavy metals, certain foods and food additives, pesticides, industrial and/or cleaning solvents, cosmetics, and some naturally occurring substances. Symptoms may appear immediately after exposure or be delayed. They may include limb weakness or numbness, loss of memory, vision, and/or intellect, uncontrollable obsessive and/or compulsive behaviors, delusions, headache, cognitive and behavioral problems and sexual dysfunction. Individuals with certain disorders may be especially vulnerable to neurotoxins.

Cisplatin, carboplatin, and oxaliplatin anticancer drugs are commonly used to treat lung, colorectal, ovarian, breast, head and neck, and genitourinary cancers. However, the efficacy of platinum-based drugs is often compromised because of the substantial risk for severe toxicities, including neurotoxicity. Neurotoxicity can result in both acute and chronic debilitation. Moreover, colorectal cancer patients treated with oxaliplatin discontinue therapy more often because of peripheral neuropathy than tumor progression, potentially compromising patient benefit.

Neurotoxicity may be diagnosed by methods known in the art including by toxicological and neurological testing such as those described by McWhinney, et al., Mol Cancer Ther Jan. 1 2009 (8) (1) 10-16; DOI: 10.1158/1535-7163.MCT-08-0840, *Platinum neurotoxicity pharmacogenetics* hereby incorporated by reference. In some embodiments, a cis-diamine Pt(II) complex of the invention will not produce substantial neurotoxicity or will exhibit 10, 20, 30, 40, 50, 60, 70, 80, 90, or 95% of the neurotoxicity of cisplatin or other anticancer drug based on equivalent dosages or on equivalent effective dosages.

Biomarkers.

Alternatively to use of $IC_{50}$ values, efficacy of treatment with a platinum(II) complex of the invention may be determined by measuring or detecting a change in one or cancer biomarkers, for example, comparing quantity of biomarkers in a blood or tissue sample before and after a treatment.

A treatment may significantly decrease the concentration of a particular biomarker, for example, by 5, 10, 15, 20, 25, 30, 35, 40, 45, 50, 55, 60, 65, 70, 75, 80, 85, 90, or 100%, compared to a control or pre-treatment value. As used herein, the term "biomarker" refers to a characteristic that is objectively measured and evaluated as an indicator of normal biological processes, pathogenic processes or pharmacological responses to a therapeutic intervention. Biomarkers include ER/PR, HER-2/neu for breast cancer, EGFR, KRAS, UGT1A1 for colorectal cancer, EML4/ALK, EGFR, and KRAS for lung cancer as well as other biomarkers described and incorporated by reference to https://_en.wikipedia.org/wiki/Cancer_biomarkers (last accessed Oct. 5, 2017). Cancer biomarkers are useful in determining the aggressiveness of an identified cancer as well as its likelihood of responding to the treatment. Examples of such prognostic biomarkers include, without limitation, CA 125, β2-microglobulin, and EBV DNA. A change or mutation in a biomarker may be detected with a polymerase chain reaction (PCR) assay, DNA microarray, multiplex ligation-dependent probe amplification (MLPA), single strand conformational polymorphism (SSCP), denaturing gradient gel electrophoresis (DGGE), heteroduplex analysis, and restriction fragment length polymorphism (RFLP). The procedures to detect the mutation are well-known to those of ordinary skill in the art. The concentration of the biomarker may be measured with an assay, for example an antibody-based method (e.g., an ELISA). As used herein, the term antibody-based method refers to any method with the use of an antibody including, but not limited to, enzyme-linked immunosorbent assay (ELISA), Western blotting, immunoprecipitation (IP), enzyme linked immunospot (ELISPOT), immunostaining, immunohistochemistry, immunocytochemistry, affinity chromatography, and the like. Preferably, an ELISA is used. The term ELISA refers to a method of detecting the presence and concentration of a biomarker in a sample, for example, before, during or after treatment with a cis-diamine Pt(II) thione complex of the invention. There are several variants of ELISA, including, but not limited to, sandwich ELISA, competitive ELISA, indirect ELISA, ELISA reverse, and the like. The ELISA assay may be a singleplex assay or a multiplex assay, which refers to a type of assay that simultaneously measures multiple analytes in a single run/cycle of the assay. Preferably, a sandwich ELISA is used. The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences. The term sample includes any biological sample taken from the subject including a cell, tissue sample, or body fluid. For example, a sample may include a tumor sample, skin sample, a cheek cell sample, saliva, or blood cells. A sample can include, without limitation, a single cell, multiple cells, fragments of cells, an aliquot of a body fluid, whole blood, platelets, serum, plasma, red blood cells, white blood cells, endothelial cells, tissue biopsies, synovial fluid, and lymphatic fluid. In some embodiments, the sample is taken from a tumor. In some embodiments, the concentration of the biomarker is measured before and after the administration. When the concentration of the biomarker is maintained, the method may further comprise increasing the effective amount of at least one of the cis-diamine platinum (II) complex of the invention, the salt thereof, the solvate thereof, the prodrug thereof, and the combination thereof by at least 5%, at least 10%, or at least 30%, up to 50%, up to 60%, or up to 80% of an initial effective amount that is in a range of 1-100 mg/kg based on the weight of the subject. The subject may be administered with the increased dosage for a longer period (e.g. 1 week more, 2 weeks more, or 2 months more) than the duration with the initial effective amount. In some embodiments, the mutation in the biomarker is detected before administrating the composition to identify subjects predisposed to the disease. For example, women with a BRCA1 germline mutation are at a higher risk of contracting ovarian cancer. In some embodiments, the biomarkers are measured/detected after each administration. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

Cancers/Proliferative Disorders.

Cancers include but are not limited to sarcomas, carcinomas, melanomas, myelomas, gliomas and lymphoma (including Hodkin lymphoma) subject to treatment or prevention with the cis-diamine platinum(II) thione complexes provided herein. In some embodiments, the cis-diamine Pt(II) thione complexes of the invention retain anti-cancer activity against cancer cells that are or have become resistant to conventional anti-cancer drugs such as cisplatin. When resistance develops to a conventional anticancer drug, treatment may be continued with a cis-diamine Pt(II) thione complex of the invention to which the cancer cells are sensitive. Sensitivity of a particular kind of cancer or proliferative disease, disorder or condition to a particular cis-diamine Pt(II) thione complex may be determined by methods known in the art.

In some embodiments, methods incorporating the use a cis-diamine platinum(II) thione complex of the present disclosure to treat or prevent cancer of the blood, brain, bladder, lung, cervix, ovary, colon, rectum, pancreas, skin, prostate gland, stomach, breast, liver, spleen, kidney, head, neck, testicle, bone, bone marrow, thyroid gland or central nervous system. In some embodiments, these methods are effective in the treatment or prevention of cervical, colon, prostate, and lung cancers. Cancers or tumor resistant to other anticancer drugs, such as cisplatin-resistant cancers, may be treated. In treating certain cancers, the best approach is often a combination of surgery, radiotherapy, and/or chemotherapy. Therefore, in at least one embodiment, the composition is employed in conjunction with conventional radiotherapy and/or chemotherapy. In another embodiment, the composition is employed with surgery. The radiotherapy and/or surgery may be before or after the composition is administered.

Other non-cancerous proliferative diseases, disorders or conditions may also be treated, such as atherosclerosis, rheumatoid arthritis, psoriasis, idiopathic pulmonary fibrosis, scleroderma, cirrhosis of the liver, or benign proliferative conditions such as verruca (warts), dermatitis, or other disorders characterized by epidermal cell proliferation.

Colon cancer, bowel cancer, or colorectal cancer develops and manifests in the colon and rectum which are parts of the large intestine. Colon cancers represent abnormal growth of cells that have the ability to invade or spread to other parts of the body. Signs and symptoms may include blood in the stool, a change in bowel movements, weight loss, and feeling tired all the time. Most colorectal cancers are associated with old age and can occur in subjects 50, 55, 60, 65, 70, 75, 80 or more years of age. Colon cancer is also associated with lifestyle factors and some cases are associated with genetic risks. Risk factors include diet, obesity, smoking, and lack of physical activity. Dietary factors that increase the risk include red and processed meat as well as alcohol. Another risk factor is inflammatory bowel disease, which includes Crohn's disease and ulcerative colitis. Some of the inherited genetic disorders that can cause colorectal cancer include familial adenomatous polyposis and hereditary non-polyposis colon cancer. Colon cancer often starts as a benign tumor, often in the form of a polyp, which over time becomes cancerous. The most common metastasis sites for colorectal cancer are the liver, the lung and the peritoneum. Treatments used for colorectal cancer may often include a combination of surgery, radiation therapy, chemotherapy and targeted therapy.

Lung cancer or lung carcinoma is a malignant lung tumor characterized by uncontrolled cell growth in tissues of the lung and can metastasize to nearby and distant tissues. Most cancers that start in the lung, known as primary lung cancers, are carcinomas and the two main types are small-cell lung carcinoma (SCLC) and non-small-cell lung carcinoma (NSCLC). The most common symptoms are coughing (including coughing up blood), weight loss, shortness of breath, and chest pains. The vast majority (85%) of cases of lung cancer are due to long-term tobacco smoking, however some cases are associated with or caused by combination of genetic factors and exposure to environmental factors such as radon gas, asbestos, second-hand smoke, or other forms of air pollution. Lung cancer may be seen on chest radiographs and computed tomography (CT) scans and diagnosis is usually confirmed by biopsy which is usually performed by bronchoscopy or CT-guidance. Common treatments include surgery, chemotherapy, and radiotherapy. NSCLC is sometimes treated with surgery, whereas SCLC usually responds better to chemotherapy and radiotherapy.

Breast cancer is cancer that develops from breast tissue. Signs of breast cancer may include a lump in the breast, a change in breast shape, dimpling of the skin, fluid coming from the nipple, or a red scaly patch of skin In breast cancers with distant spread of the disease, there may be bone pain, swollen lymph nodes, shortness of breath, or yellow skin. Risk factors for developing breast cancer include being female, obesity, lack of physical exercise, drinking alcohol, hormone replacement therapy during menopause, ionizing radiation, early age at first menstruation, having children late or not at all, older age, and family history. About 5-10% of cases are due to genes inherited from a person's parents, including BRCA1 and BRCA2 among others. The cis-diamine Pt(II) thione complex of the invention may be administered by itself or in combination with other therapy to a subject at risk of breast cancer, a subject diagnosed with breast cancer, or a subject under treatment for breast cancer, or a subject who has already been treated for breast cancer, for example, by removal of breast tissue.

Therapy.

As used herein, the terms "therapies" and "therapy" can refer to any method, composition, and/or active ingredient that can be used in the treatment and/or management of the disease or one or more symptoms thereof. In some embodiments, the method for treating the disease involves the administration of a unit dosage or a therapeutically effective amount of the active ingredient to a subject in need thereof.

Administration.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection including intravenous, subcutaneous, intraperitoneal, intramuscular, intravascular, or infusion, topical and rectal administration. Those of ordinary skill in the art are familiar with administration techniques that can be employed with the compounds and methods described herein. In preferred embodiments, the active ingredient and/or the composition described herein are administered orally.

The terms "effective amount", "therapeutically effective amount", or "pharmaceutically effective amount" refer to that amount of the active ingredient being administered which will relieve to some extent one or more of the symptoms of the disease being treated. The result can be reduction and/or alleviation of the signs, symptoms, or causes of a disease, or any other desired alteration of a biological system. For example, an "effective amount" for therapeutic uses is the amount of the cis-diamine platinum (II) complex of the invention, the salt thereof, the solvate thereof, the prodrug thereof, or a combination thereof as disclosed herein required to provide a clinically significant decrease in a disease. An appropriate "effective amount" may differ from one individual to another. An appropriate "effective amount" in any individual case may be determined using techniques, such as a dose escalation study.

The dosage and treatment duration are dependent on factors, such as bioavailability of a drug, administration mode, toxicity of a drug, gender, age, lifestyle, body weight, the use of other drugs and dietary supplements, the disease stage, or tolerance and resistance of the body to the administered drug, and then determined and adjusted accordingly. In at least one embodiment, the at least one of the cis-diamine platinum(II) complex of the invention, the salt thereof, the solvate thereof, the prodrug thereof, and the combination thereof is administered in an effective amount in a range of 1-100 mg/kg based on the weight of the subject, preferably 10-80 mg/kg, more preferably 20-50 mg/kg.

In some embodiments, a treatment will involve administering a composition comprising at least 0.5 wt %, 5 wt %, 10 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, 95 wt %, 99 wt %, or 99.9 wt %, of the cis-diamine platinum(II) complex of the invention. The composition may comprise 0.01-50 µM, 0.01-30 µM, preferably 0.01-10 µM of the cis-diamine platinum(II) thione complex of the invention relative to the total composition. In some embodiments, the composition comprises up to 0.1 wt %, 1 wt %, 5 wt %, or 10 wt % of the pharmaceutically acceptable salt of the cis-diamine platinum(II) thione complex of the invention. In some embodiments, the composition comprises up to 0.1 wt %, 1 wt %, 5 wt %, or 10 wt % of the pharmaceutically acceptable solvate thereof of either the cis-diamine platinum (II) complex of the invention. These ranges include all intermediate subranges and values.

A treatment method may comprise administering a composition containing the cis-diamine platinum(II) thione complex of the invention as a single dose or multiple individual divided doses. In some embodiments, the composition is administered at various dosages (e.g., a first dose with an effective amount of 50 mg/kg and a second dose with an effective amount of 10 mg/kg). In some embodiments, the interval of time between the administration of the composition and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 1 months, 12 months, 1 year, 2 years, or any period of time in between. Preferably, the composition is administered once daily for at least 2 days, 5 days, 6 days, or 7 days. In certain embodiments, the composition and one or more additional therapies are administered less than 1 day, 1 week, 2 weeks, 3 weeks, 4 weeks, one month, 2 months, 3 months, 6 months, 1 year, 2 years, or 5 years apart.

EMBODIMENTS

The following examples illustrate various aspects of the present invention. They are not to be construed to limit the claims in any manner whatsoever.

1. A method for treating a proliferative disease, disorder, or condition comprising administering to a subject in need thereof a complex comprising the formula [Pt(N R$_1$R2)$_2$ (Thione)$_2$].2[anion]; wherein R$_1$ and R$_2$ are, independently, hydrogen, alkyl or aryl.

2. The method of embodiment 1, wherein the thione molecule used to produce the complex is selected from the group consisting of:

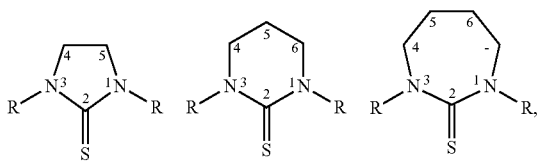

wherein, R, independently, is H, alkyl, or aryl which may be further substituted.

3. The method of embodiment 1, wherein the thione molecule used to produce the complex is selected from the group consisting of:

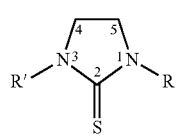
(a-g)

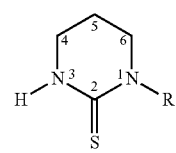
(h-i)

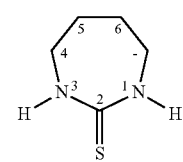
(j)

wherein in (a) R═R'═H; (b) R═H, R'═CH$_3$; (c) R═CH$_3$, R'═CH$_3$; (d) R═R' ═C$_2$H$_5$; (e) R═H, R'═C$_3$H$_7$; (f) R═H, R'═i-C$_3$H$_7$; (g) R═R'═i-C$_3$H$_7$; (h) R═H; (i) R C$_2$H$_5$; and (j) is 1,3-Diazepane-2-thione (Diap).

4. The method of embodiment 1, wherein the platinum (II) complex has the formula Pt(NH$_3$)$_2$(Thione)$_2$.2NO$_3$ or a variant complex wherein one or two of the NO$_3$ anions are replaced with one or more different anions.

5. The method of embodiment 1, wherein the complex is selected from the group consisting of at least one of cis-[Pt (NH$_3$)$_2$(Imt)$_2$].2NO$_3$ (1), cis-[Pt(NH$_3$)$_2$(MeImt)$_2$].2NO$_3$ (2), cis-[Pt(NH$_3$)$_2$(Me$_2$Imt)$_2$].2NO$_3$ (3), cis-[Pt(NH$_3$)$_2$(Et$_2$Imt)$_2$] .2NO$_3$ (4), cis-[Pt(NH$_3$)$_2$(PrImt)$_2$].2NO$_3$ (5), cis-[Pt(NH$_3$)$_2$ (iPrImt)$_2$].2NO$_3$ (6), cis-[Pt(NH$_3$)$_2$(iPr$_2$Imt)$_2$].2NO$_3$ (7), cis-[Pt(NH$_3$)$_2$(Diaz)$_2$].2NO$_3$ (8), cis-[Pt(NH$_3$)$_2$(EtDiaz)$_2$].2NO$_3$ (9), and cis-[Pt(NH$_3$)$_2$(Diap)$_2$].2NO$_3$ (10), or a variant complex wherein one or two of the NO$_3$ anions are replaced with one or more different anions.

6. The method of embodiment 5, wherein in said cis-diamine platinum(II) thione complex both anions are NO$_3$.

7. The method of embodiment 1, wherein the proliferative disease, disorder or condition is cancer.

8. The method of embodiment 1, wherein the proliferative disease, disorder or condition is not cancer.

9. The method of claim 1, wherein the proliferative disease, disorder or condition is cancer that is or has become resistant to cisplatin or wherein the cis-diamine Pt(II) thione complex produces less nephrotoxicity or neurotoxicity that the same dose of cisplatin.

10. The method of embodiment 1, wherein the proliferative disease, disorder, or condition is breast cancer.

11. The method of embodiment 1, wherein the proliferative disease, disorder, or condition is colon cancer.

12. The method of embodiment 1, wherein the proliferative disease, disorder, or condition is lung cancer.

13. A cis-diamine platinum(II) thione complex comprising the formula [Pt(N R$_1$R$_2$)$_2$(Thione)$_2$].2[anion]; wherein R$_1$ and R$_2$ are, independently, hydrogen, alkyl or aryl.

14. The cis-diamine platinum(II) thione complex of embodiment 12, wherein the thione molecule used to produce the complex is selected from the group consisting of:

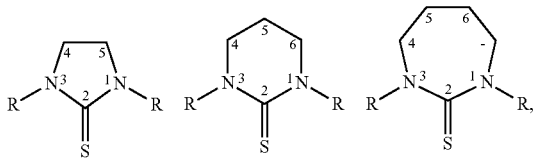

wherein R, independently, is H, alkyl, or aryl.

15. The cis-diamine platinum(II) thione complex of embodiment 14, wherein the thione molecule used to produce the complex is selected from the group consisting of:

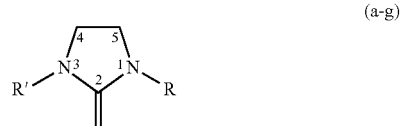
(a-g)

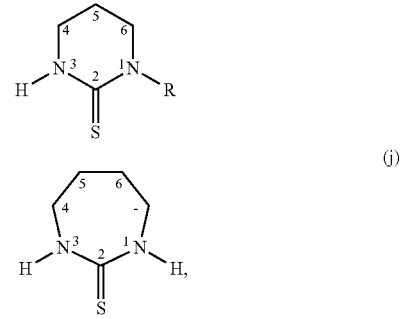
(h-i)

(j)

wherein in (a) R═R'═H; (b) R═H, R'═CH$_3$; (c) R═CH$_3$, R'═CH$_3$; (d) R═R'═C$_2$H$_5$; (e) R═H, R'═C$_3$H$_7$; (f) R═H, R'═i-C$_3$H$_7$; (g) R═R'═i-C$_3$H$_7$; (h) R═H; (i) R═C$_2$H$_5$; and (j) is 1,3-Diazepane-2-thione (Diap).

16. The cis-diamine platinum(II) thione complex of embodiment 14, wherein the platinum (II) complex has the formula Pt(NH$_3$)$_2$(Thione)$_2$.2NO$_3$ or a variant complex wherein one or two of the NO$_3$ anions are replaced with one or more different anions.

17. The cis-diamine platinum(II) thione complex of embodiment 14, wherein the complex is selected from the group consisting of at least one of cis-[Pt(NH$_3$)$_2$(Imt)$_2$]. 2NO$_3$ (1), cis-[Pt(NH$_3$)$_2$(MeImt)$_2$].2NO$_3$ (2), cis-[Pt(NH$_3$)$_2$ (Me$_2$Imt)$_2$].2NO$_3$ (3), cis-[Pt(NH$_3$)$_2$(Et$_2$Imt)$_2$].2NO$_3$ (4), cis-[Pt(NH$_3$)$_2$(PrImt)$_2$].2NO$_3$ (5), cis-[Pt(NH$_3$)$_2$(iPrImt)$_2$]. 2NO$_3$ (6), cis-[Pt(NH$_3$)$_2$(iPr$_2$Imt)$_2$].2NO$_3$ (7), cis-[Pt(NH$_3$)$_2$ (Diaz)$_2$].2NO$_3$ (8), cis-[Pt(NH$_3$)$_2$(EtDiaz)$_2$].2NO$_3$ (9), and cis-[Pt(NH$_3$)$_2$(Diap)$_2$].2NO$_3$ (10), or a variant complex wherein one or two of the NO$_3$ anions are replaced with one or more different anions.

18. The cis-diamine platinum(II) thione complex of embodiment 14, wherein both anions are NO$_3$.

19. A pharmaceutical composition comprising at least one cis-diamine platinum(II) thione complex of embodiment 13 in combination with at least one pharmaceutically acceptable carrier or excipient.

20. The pharmaceutical composition of embodiment 19 that further comprises another anticancer drug, chemotherapeutic agent, or immunopotentiator.

EXAMPLES

Example 1

Synthesis of cis-[Pt(NH$_3$)$_2$L$_2$].2NO$_3$ Complexes (1-10)

Cisplatin was obtained from Strem Chemical Company, USA. Dimethylsulfoxide-d$_6$ and D$_2$O were purchased from Fluka Chemical Co. The thione ligands were prepared according to the procedure mentioned in the literature. See S. Ahmad, A. A. Isab, H. P. Perzanowski. Can. J. Chem. 80 (2002) 1279-1284; and A. A. Isab, S. Ahmad, M. Arab, Polyhedron 21 (2002)$_{1267}$-1271, each incorporated herein by reference in their entirety. (3-(4,5-Dimethylthiazol-2-yl)-2, 5-diphenyltetrazolium bromide, a yellow tetrazole) was purchased from Sigma Chemical Co, St. Louis, Mo., USA.

Compounds 1-10 were prepared by adding 0.17 g (1.0 mmol) AgNO$_3$ to the solutions containing (0.15 g, 0.5 mmol) of cis-diaminedichloridoplatinum(II) (cisplatin) in 10 mL water and stirring the mixture for one hour in the dark at room temperature. The solution was filtered to remove silver chloride as solid. Then 1.0 mmol of thione ligands dissolved in 10 mL methanol was added to the filtrates dropwise. After stirring the solution for one hour it was filtered and kept at room temperature. Solid powders were obtained on slow evaporation of the solvent. The CHNS data, melting/decomposition points, and % yield of the synthesized complexes are presented below:

cis-[Pt(NH)$_2$(Imt)$_2$].2NO$_3$ (1)

M. p. 130-132° C.; Yield 0.248 g, 89%; Analysis. Calc.: C12.93%, H3.25%, N20.10, S 11.50%; Found: C12.48%, H3.56%, N20.26%, S 11.37%. IR (v, cm$^{-1}$): 3376 (s), 1036 (s), 494 (s), 827 (8, s), 273 (s).

cis-[Pt(NH$_3$)$_2$(MeImt)$_2$].2NO$_3$ (2)

M. p. 126-128° C.; Yield 0.213 g, 73%; Analysis. Calc.: C16.41%, H3.79%, N19.14, S 10.95%; Found: C16.46%, H3.73%, N19.06%, S 11.06%. IR (v, cm$^{-1}$): 3481 (s), 1028 (s), 501 (s), 823 (8, s), 287 (s).

cis-[Pt(NH$_3$)$_2$(Me$_2$Imt)$_2$].2NO$_3$ (3)

M. p. 73-75° C.; Yield 0.214 g, 70%; Analysis. Calc.: C19.57%, H4.27%, N18.16, S 10.45%; Found: C19.41%, H4.22%, N18.10%, S 10.34%. IR (v, cm$^{-1}$): 1118 (s), 491 (s), 825 (8, s), 280 (s).

cis-[Pt(NH$_3$)$_2$(Et$_2$Imt)$_2$].2NO$_3$ (4)

M. p. 111-113° C.; Yield 0.211 g, 64%; Analysis. Calc.: C25.11%, H5.12%, N16.73, S 9.58%; Found: C25.41%, H5.22%, N16.97%, S 9.84%. IR (v, cm$^{-1}$): 1079 (s), 492 (s), 837 (8, s), 268 (s).

cis-[Pt(NH$_3$)$_2$(PrImt)$_2$].2NO$_3$ (5)

M. p. 125-127° C.; Yield 0.231 g, 72%; Analysis. Calc.: C22.46%, H4.71%, N17.48, S 9.99%; Found: C22.04%, H4.88%, N17.21%, S 10.07%. IR (v, cm$^{-1}$): 3462 (s), 1048 (s), 501 (s), 827 (8, s), 282 (s).

cis-[Pt(NH$_3$)$_2$(iPrImt)$_2$].2NO$_3$ (6)

M. p. 138-140° C.; Yield 0.263 g, 82%; Analysis. Calc.: C22.46%, H4.71%, N17.48, S 9.99%; Found: C21.99%, H4.49%, N17.35%, S 9.62%. IR (v, cm$^{-i}$): 1078 (s), 508 (s), 840 (6, s), 283 (s).

cis-[Pt(NH$_3$)$_2$(iPr$_2$Imt)$_2$].2NO$_3$ (7)

M. p. 119-121° C.; Yield 0.178 g, 49%; Analysis. Calc.: C29.79%, H5.83%, N15.44, S 8.84%; Found: C29.29%, H5.62%, N15.65%, S 8.77%. IR (v, cm$^{-1}$): 1062 (s), 520 (s), 824 (8, s), 274 (s).

cis-[Pt(NH$_3$)$_2$(Diaz)$_2$].2NO$_3$ (8)

M. p. 112-114° C.; Yield 0.254 g, 87%; Analysis. Calc.: C16.41%, H3.79%, N19.14, S 10.95%; Found: C16.78%, H3.92%, N19.45%, S 10.89%. IR (v, cm$^{-1}$): 3459 (s), 1070 (s), 507 (s), 811 (8, s), 268 (s).

cis-[Pt(NH$_3$)$_2$(EtDiaz)$_2$].2NO$_3$ (9)

M. p. 86-88° C.; Yield 0.211 g, 66%; Analysis. Calc.: C22.46%, H4.71%, N17.48, S 9.99%; Found: C22.32%, H4.47%, N17.53%, S 9.68%. IR (v, cm$^{-1}$): 3428 (s), 1121 (s), 499 (s), 827 (6, s), 291 (s).

cis-[Pt(NH$_3$)$_2$(Diap)$_2$].2NO$_3$ (10)

M. p. 155-157° C.; Yield 0.274, 89%; Analysis. Calc.: C19.57%, H4.27%, N18.26, S 10.45%, Found: C18.89%, H4.34%, N18.67%, S 10.49%. IR (v, cm$^{-1}$): 3237 (s), 1066 (s), 502 (s), 824 (8, s), 276 (s).

Synthesis.

For the preparation of complexes, cisplatin was first converted into nitrate form by addition of two equivalents of AgNO$_3$ to cisplatin. The nitrate species was then reacted with thione (L) ligands in a 1:2 molar ratio. The reaction yielded the colored complexes of the general formula, cis-[Pt(NH$_3$)$_2$(L)$_2$].2NO$_3$ in high yields. The observed values of elemental (CHNS) analysis of these complexes are consistent with the suggested compositions.

Example 2

Spectroscopic Measurements

Elemental analysis of carbon, hydrogen, nitrogen and sulfur were performed on Perkin Elmer Series 11 (CHNS/O), Analyzer 2400. The solid state FTIR spectra of the ligands and their platinum(II) complexes were recorded on a NICOLET 6700 FTIR using diamond ATR over the range 4000-400 cm$^{-1}$.

The $^1$H and $^{13}$C NMR spectra in DMSO-d$_6$ and D$_2$O were carried out on a JEOL JNM-LA 500 NMR spectrometer at 500.00 MHz and 125.65 MHz operating frequency respectively. The $^{13}$C NMR spectra were recorded with $^1$H broadband decoupling at 297 K. The conditions of the spectral were 32 K data points, 0.963 acquisition time, 3.2 s pulse delay and a 5.75 μs pulse width for $^1$H NMR, and 32 K data points, 0.963 s acquisition time, 2.5 s pulse delay and a 5.12 μs pulse width for $^{13}$C NMR. The chemical shifts were measured relative to Tetramethylsilane (TMS).

IR Spectroscopy.

The selected Infrared absorption frequencies of the free ligands and their platinum(II) compounds are listed in Table SI. Three characteristic vibrational bands are usually observed in the IR spectra of thione complexes, which include, ν(C=S) vibration, which occurs around 1200 and 600 cm$^{-i}$, the N—H stretching near 3200 cm$^{-1}$ and M-sulfur stretching band. The presence of ν(N—H) and ν(C=S) bands in all complexes prove the presence of thione ligands in the complexes in the solid state. The spectra of all free ligands display a band around 600 cm$^{-1}$ as well as 1200 cm$^{-1}$ that belong to ν(C=S) stretching. See, S. Ahmad et al.; A. A. Isab et al.; and B. P. Kennedy, A. B. P. Lever, Can. J. Chem. 50 (1972) 3488-3507, each incorporated herein by reference in their entirety. These bands shifted toward lower wave number upon complexation in agreement with our suggestion that sulfur atom is bonded to metal centre and the double bond character of C=S bond has been reduced. In order to investigate metal-sulfur stretching frequencies of the synthesized complexes, the spectra were recorded in the far-infrared region below 400 cm$^{-1}$. This band lies in the range of about 300 cm$^{-1}$ for the transition-metal complexes according to the literature. See D. M. Adam, J. B. Cornell. J. Chem. Soc. (1967) 884-889, incorporated herein by reference in its entirety. In all complexes, we observed a sharp peak around 280 cm$^{-1}$ that was assigned to platinum-sulfur bond.

A sharp band around 825 cm$^{-1}$ for all cis-[Pt(NH$_3$)$_2$(L)$_2$].2NO$_3$ complexes and its absence in the free ligand spectra is attributed to the presence of non-coordinated nitrate ion. See A. A. Isab et al., incorporated herein by reference in its entirety.

$^1$H and $^{13}$C NMR Spectroscopy. All the signals of thione ligands detected in the $^1$H and $^{13}$C NMR spectra of uncomplexed molecules were also found in the spectra of the Pt(II) complexes, which are summarized in Tables I and 2 respectively. Upon coordination, the N—H signal of thiones become less intense and shifted upfield by 0.64-1.14 ppm with respect to their positions in free ligands. The deshielding of the N—H proton is related to an increase in π electron density in the C—N bond upon complexation, which indicates that the ligands are coordinated to the platinum centre through the sulfur atom and not via nitrogen. See J. Zisowsky et al., incorporated herein by reference in its entirety.

In $^{13}$C NMR, the C=S resonance of thiones shifted upfield by 5.5-11.1 ppm upon complexation compared to its position in free ligands. This shift is associated with a decrease in the bond order of C=S bond upon coordination and a shift of N→C electron density, producing a partial double bond character in the C—N bond. See. S. Ahmad et al.; and A. A. Isab et al., each incorporated herein by reference in their entirety. The shift difference in the thiocarbonyl resonance may be related to the strength of metal-sulfur bond. See Z. Popovic, G. Pavlovic, D. Matkovic-Calogovic, Z. Soldin, M. Rajic, D. Vikic-Topic, D. Kovacek, Inorg. Chim. Acta 306 (2000) 142, incorporated herein by reference in its entirety. The data shows that the Me$_2$Imt complex with the most significant shift of 13.57 ppm forms the most stable complex. As observed previously, changing the group at the N-1 position has a little effect on the C-2 shift. See S. Ahmad et al., incorporated herein by reference in its entirety. However, in going from Imt to MeImt and Me$_2$Imt complex a little downfield shift is observed. In the complexes of Imt and its derivatives a deshielding effect is observed at C-4/5, while in Diaz and EtDiaz complexes, a deshielding effect is observed at C-4 and C-6, but C-5 bears a shielding effect. The deshielding at C-4/6 is due to an increase in p character of the C—N bond.

TABLE 1

$^1$H chemical shifts (ppm) for the ligands and their cis-Pt(II) complexes in DMSO-d$_6$.

| Species | N-H | H-4 | H-5 | H-6 | N-C1 | N-C2 | N-C3 |
|---|---|---|---|---|---|---|---|
| Imt | 7.90 | s, 4H, 3.59 | s, 4H, 3.59 | — | — | — | — |
| 1 | 9.04 | s, 4H, 3.68 | s, 4H, 3.68 | — | — | — | — |
| MeImt | 7.93 | t, 2H, 3.63 | t, 2H, 3.43 | — | s, 3H, 2.92 | — | — |
| 2 | 8.82 | t, 2H, 3.75 | t, 2H, 3.58 | — | s, 3H, 2.98 | — | — |
| Me$_2$Imt | — | s, 4H, 3.48 | s, 4H, 3.48 | — | s, 6H, 2.91 | — | — |
| 3 | — | s, 4H, 3.67 | s, 4H, 3.67 | — | s, 6H, 3.18 | — | — |
| Et$_2$Imt | — | s, 4H, 3.48 | s, 4H, 3.48 | — | q, 4H, 3.37 | t, 6H, 0.97 | — |
| 4 | — | s, 4H, 3.48 | s, 4H, 3.48 | — | q, 4H, 3.37 | t, 6H, 0.97 | — |
| PrImt | 7.99 | t, 2H, 3.58 | t, 2H, 3.41 | — | t, 2H, 3.31 | m, 2H, 1.45 | t, 3H, 0.73 |
| 5 | 8.63 | t, 2H, 3.73 | t, 2H, 3.59 | — | t, 2H, 3.36 | m, 2H, 1.52 | t, 3H, 0.76 |
| iPrImt | 7.96 | t, 2H, 3.53 | t, 2H, 3.38 | — | m, 1H, 4.35 | d, 6H, 1.00 | — |
| 6 | 8.77 | t, 2H, 3.68 | t, 2H, 3.57 | — | m, 1H, 4.30 | d, 6H, 1.06 | — |
| iPr$_2$Imt | — | s, 4H, 3.22 | s, 4H, 3.22 | — | m, 1H, 4.48 | d, 6H, 0.99 | — |
| 7 | — | s, 4H, 3.41 | s, 4H, 3.41 | — | m, 1H, 4.46 | d, 6H, 0.99 | — |
| Diaz | 7.77 | t, 4H, 3.15 | m, 2H, 1.75 | t, 4H, 3.15 | — | — | — |
| 8 | 8.83 | 4H, 3.2 | m, 2H, 1.74 | 4H, 3.2 | — | — | — |
| EtDiaz | 7.70 | t, 2H, 3.62 | m, 2H, 1.83 | t, 2H, 3.28 | q, 2H, 3.12 | t, 3H, 1.02 | — |
| 9 | 8.44 | t, 2H, 3.56 | m, 2H, 1.85 | t, 2H, 3.34 | q, 2H, 3.27 | t, 3H, 1.05 | — |
| Diap | 7.70 | t, 4H, 3.18 | t, 4H, 1.67 | t, 4H, 1.67 | — | — | — |
| 10 | 8.74 | t, 4H, 3.20 | t, 4H, 1.62 | t, 4H, 1.62 | — | — | — | s: singlet, d: doublet, t: triplet, q: quartet; m: multiplet

TABLE 2

$^1$H and $^{13}$C chemical shifts (ppm) for the ligands and their cis-Pt(II) complexes in D$_2$0

| Species | C-2 | C-4 | C-5 | C-6 | N-C1 | N-C2 | N-C3 |
|---|---|---|---|---|---|---|---|
| Imt | 182.11 | 45.38 | 45.38 | — | — | — | — |
| 1 | 174.89 | 45.96 | 45.96 | — | — | — | — |
| MeImt | 181.38 | 42.00 | 51.82 | — | 34.35 | — | — |
| 2 | 173.92 | 42.88 | 52.50 | — | 34.07 | — | — |
| Me$_2$Imt | 180.46 | 48.73 | 48.73 | — | 34.80 | — | — |
| 3 | 166.89 | 50.29 | 50.29 | — | 36.07 | — | — |
| Et$_2$Imt | 178.74 | 46.13 | 46.13 | — | 42.69 | 11.92 | — |
| 4 | 170.95 | 47.32 | 47.32 | — | 43.73 | 12.10 | — |
| PrImt | 180.87 | 49.14 | 48.86 | 42.11 | 20.65 | 11.09 | 11.09 |
| 5 | 169.74 | 50.02 | 48.92 | — | 42.97 | 20.64 | 10.95 |

TABLE 2-continued $^1$H and $^{13}$C chemical shifts (ppm) for the ligands and their cis-Pt(II) complexes in $D_2O$

| Species | C-2 | C-4 | C-5 | C-6 | N-C1 | N-C2 | N-C3 |
|---|---|---|---|---|---|---|---|
| iPrImt | 179.70 | 42.21 | 43.73 | — | 48.18 | 19.55 | — |
| 6 | 172.60 | 42.94 | 44.69 | — | 48.90 | 19.23 | — |
| iPr$_2$Imt | 171.05 | 48.25 | 48.25 | — | 41.52 | 19.10 | — |
| 7 | 165.55 | 48.86 | 48.86 | — | 41.22 | 18.94 | — |
| Diaz | 173.34 | 41.00 | 19.25 | 41.00 | — | — | — |
| 8 | 166.78 | 41.03 | 18.86 | 41.03 | — | — | — |
| EtDiaz | 173.36 | 41.14 | 20.93 | 46.14 | 49.54 | 12.33 | — |
| 9 | 165.54 | 41.38 | 20.31 | 47.53 | 49.61 | 12.51 | — |
| Diap | 183.99 | 45.86 | 26.99 | 26.99 | — | — | — |
| 10 | 177.29 | 47.20 | 26.80 | 26.80 | — | — | — |

Example 3

In Vitro Cytotoxic Activity Against, AS49, MCF7 and HTC15 Human Cancer Cell Lines The cis-[Pt(NH$_3$)$_2$(thione)$_2$].2NO$_3$ complexes were evaluated for their in vitro cytotoxic activity against A549 (human lung cancer), MCF-7 (human breast cancer) and HTC15 (human colon cancer) cell lines. The cells were seeded at 4×10$^3$ cells/well in 100 μL DMEM containing 10% FBS in 96-wells tissue culture plate and incubated for 72 h at 37° C., 5% CO$_2$ in the air and 90% relative humidity in the CO$_2$ incubator. After incubation, 100 μL of each sample solution (50, 25, 12.5 and 6.25 μM), prepared in DMEM, were added to cells and the cultures were incubated for 24 h. The medium of wells was discarded and 100 μL DMEM containing MTT (3-(4,5-Dimethylthiazol-2-yl)-2,5-diphenyltetrazolium Bromide) (5 mg/mL) was added to the wells and incubated in a CO$_2$ incubator at 37° C. in dark for 4 h. After incubation, purple colored formazan (artificial chromogenic dye, a product of the reduction of water insoluble tetrazolium salts e.g., MMT by dehydrogenases and reductases) in the cells is produced and appeared as dark crystals in the bottom of the wells. The resultant crystals were solubilized by adding 100 μL of DMSO in each well. The solution was thoroughly mixed to dissolve the formazan crystals, producing a purple solution. The absorbance of the 96-wells plate was taken at 570 nm with Labsystems Multiskan EX-Enzyme-linked immunosorbent assay (EX-ELISA) reader against a reagent blank. The IC$_{50}$ values were calculated from three independent experiments by generating an equation of logarithmic trendline of percentage cell viability against concentration compounds in Microsoft excel.

Antitumor Activity.

In vitro cytotoxic properties of ten new cis-[Pt(NH$_3$)$_2$(Thione)$_2$].2NO$_3$ complexes were evaluated against three human cancer cell lines, which are: A549 (human lung carcinoma), MCF7 (human breast carcinoma), and HCT15 (human colon adenocarcinoma) cell lines and compared with cytotoxicity of cisplatin and carboplatin under the same conditions. The cytotoxicity of cisplatin, carboplatin and the complexes was obtained by the stipulated increase in their concentrations against fixed number of human cancer cells. The IC$_{50}$ values were obtained from curves between the complexes concentration and viability percentage of the cells, and are listed, in Table 3.

The IC$_{50}$ values of the complexes against A549 cell lines are in the range of 50 to 108 μM. Cisplatin was found to be the most effective for these cells. Four of the ten studied complexes, 1, 6, 7 and 10 (having the IC$_{50}$ values 53, 55, 50 and 52 μM respectively) exhibited in vitro cytotoxicity that is comparable to cisplatin but about 1-4 fold better than that of carboplatin. Moreover, the inhibition effect of complex 5, 8 and 9 is nearly same as that of carboplatin. For MCF7 cells, cisplatin is highly potent, while carboplatin, as well as the investigated complexes, displayed poor antiproliferative potency as indicated by high IC$_{50}$ values. However, one of the compounds, 3 was found to have a greater cytotoxic effect than carboplatin against this cell with IC$_{50}$ of 58 μM. Against HCT15 cell lines, all the complexes were noticed to have lower cytotoxicity than cisplatin. But, with respect to carboplatin four complexes, 5, 6, 7, 10 displayed lower IC$_{50}$ values, while complex 3 has nearly same value as carboplatin.

Figure 4A:
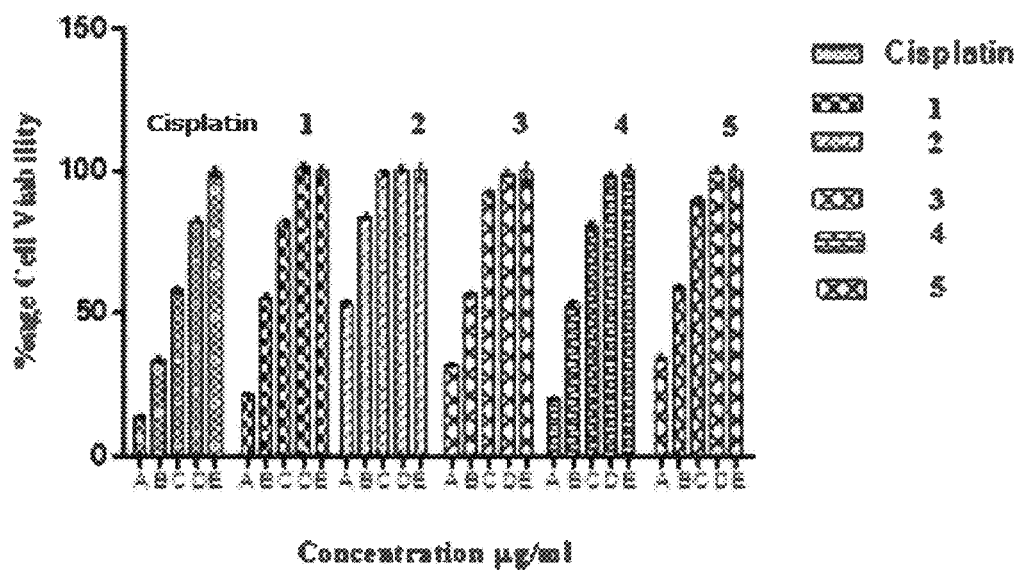

The survival of the cells (A549, MCF7 and HCT15) as a function of the concentration of compounds 1-10 is illustrated in FIGS. 4A-4B; 5A-5B, and 6A-6B which respectively show effect of concentration of complexes 1-10 on viability of A549 cells (FIG. 4A-4B), effect of concentration of complexes 1-10 on viability of MCF7 cells (FIG. 5A-5B), and Effect of concentration of complexes 1-10 on viability of HCT1 cells (FIG. 6A-6B).

TABLE 3

IC$_{50}$ Values in (μM) of prepared compounds, against four human tumor cell lines

| Compounds | A549 | MCF7 | HCT15 |
|---|---|---|---|
| Cisplatin | 42 ± 2 | 23 ± 3 | 32 ± 2 |
| Carboplatin | 70 ± 2 | 63 ± 2 | 53 ± 2 |
| 1 | 53 ± 2 | 101 ± 2 | 82 ± 1 |
| 2 | 85 ± 1 | 82 ± 1 | 75 ± 2 |
| 3 | 68 ± 1 | 58 ± 1 | 54 ± 1 |
| 4 | 108 ± 2 | 97 ± 3 | 97 ± 3 |
| 5 | 72 ± 2 | 74 ± 2 | 51 ± 2 |
| 6 | 55 ± 1 | 81 ± 3 | 48 ± 1 |
| 7 | 50 ± 2 | 78 ± 2 | 52 ± 1 |
| 8 | 75 ± 2 | 90 ± 2 | 76 ± 1 |
| 9 | 73 ± 1 | 103 ± 3 | 90 ± 2 |
| 10 | 52 ± 2 | 71 ± 1 | 41 ± 1 |

$^a$Errors are standard deviations determined from at least three independent experiments.

The experimental results are presented as the micro-mole concentration of 50% cell growth inhibition (IC$_{50}$) of each drug. The MTT assay was performed in three independent experiments, each in triplicate. The cancer cell lines used are A549 (human lung cancer), MCF-7 (human breast cancer) and HTC15 (human colon cancer) cell lines.

As shown herein, a new series of cis-diamine platinum(II) complexes (1-10) with the general formula, cis-[Pt(NH$_3$)$_2$(Thione)$_2$].2NO$_3$ have been synthesized and characterized using both elemental analysis and spectroscopic methods. The spectroscopic data strongly supported that the thione ligands are coordinated to the Pt(II) centre through the sulfur atom. In vitro cytotoxicity of some complexes demonstrated a comparable cytotoxicity to cisplatin and better than carboplatin Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the words "a" and "an" and the like carry the meaning of "one or more" unless the context clearly indicates otherwise.

Within the description of this disclosure, where a numerical limit or range is stated, the endpoints are included unless stated otherwise. Also, all values and subranges within a numerical limit or range are specifically included as if explicitly written out. For example, a range of 0 to 10 wt % includes 0. 0.25, 0.5, 1, 1.5, 2, 2.5, 3, 4, 5, 6, 7, 8, 9, 9.75, 9.99, <10, and 10.

The terms "including", "such as", "for example" and the like not intended to limit the scope of the present disclosure. They generally refer to one or more elements falling with a class or genus of other similar elements.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by insertion of a space or underlined space into a link, for example, before "www" or after "//" and may be reactivated by removal of the space.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all subranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it is also envisioned that Parameter X may have other ranges of values including 1-9, 2-9, 3-8, 1-8, 1-3, 1-2, 2-10, 2.5-7.8, 2-8, 2-3, 3-10, and 3-9, as mere examples.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for treating a proliferative disease, disorder, or condition, comprising: administering to a subject in need thereof a complex of formula [Pt(N $R_1R_2)_2$(thione)$_2$].2[anion]; wherein $R_1$ and $R_2$ are, independently, hydrogen, alkyl or aryl.

2. The method of claim 1, wherein the thione used to produce the complex is selected from the group consisting of:

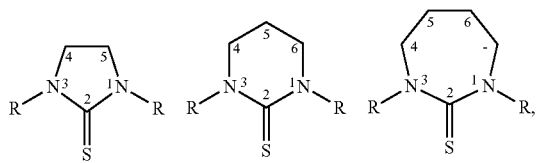

wherein each R is independently a H, alkyl, or aryl.

3. The method of claim 1, wherein the thione used to produce the complex is selected from the group consisting of:

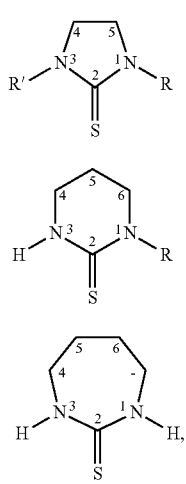

wherein in (a) R=R'=H; (b) R=H, R'=CH$_3$; (c) R=CH$_3$, R'=CH$_3$; (d) R=R'=C$_2$H$_5$; (e) R=H, R'=C$_3$H$_7$; (f) R=H, R'=i-C$_3$H$_7$; (g) R=R'=i-C$_3$H$_7$; (h) R=H; (i) R=C$_2$H$_5$; and (j) is 1,3-Diazepane-2-thione (Diap).

4. The method of claim 1, wherein the complex has the formula Pt(NH$_3$)$_2$(thione)$_2$].2NO$_3$ or a variant complex wherein one or two of the NO$_3$ anions are replaced with one or more different anions.

5. The method of claim 1, wherein the complex is selected from the group consisting of at least one of cis-[Pt(NH$_3$)$_2$(Imt)$_2$].2NO$_3$ (1), cis-[Pt(NH$_3$)$_2$(MeImt)$_2$].2NO$_3$ (2), cis-[Pt(NH$_3$)$_2$(Me$_2$Imt)$_2$].2NO$_3$ (3), cis-[Pt(NH$_3$)$_2$(Et$_2$Imt)$_2$].2NO$_3$ (4), cis-[Pt(NH$_3$)$_2$(PrImt)$_2$].2NO$_3$ (5), cis-[Pt(NH$_3$)$_2$(iPrImt)$_2$].2NO$_3$ (6), cis-[Pt(NH$_3$)$_2$(iPr$_2$Imt)$_2$].2NO$_3$ (7), cis-[Pt(NH$_3$)$_2$(Diaz)$_2$].2NO$_3$ (8), cis-[Pt(NH$_3$)$_2$(EtDiaz)$_2$].2NO$_3$ (9), and cis-[Pt(NH$_3$)$_2$(Diap)$_2$].2NO$_3$ (10), or a variant complex wherein one or two of the NO$_3$ anions are replaced with one or more different anions: wherein Imt is imidazolidine-2-thione, MeImt is N-methylimidazolidine-2-thione, Me$_2$Imt is N,N'-dimethylimidazolidine-2-thione, Et$_2$Imt is N,N'-diethylimidazolidine-2-thione, PrImt is N-propylimidazolidine-2-thione, iPrImt is N-(isopropyl)imidazolidine-2-thione, iPr$_2$Imt is N,N'-(di-isopropyl)imidazolidine-2-thione, Diaz is diazinane-2-thione, and Diap is 1,3-Diazepane-2-thione.

6. The method of claim 1, wherein the complex is selected from the group consisting of at least one of cis-[Pt(NH$_3$)$_2$(Imt)$_2$].2NO$_3$ (1), cis-[Pt(NH$_3$)$_2$(MeImt)$_2$].2NO$_3$ (2), cis-[Pt(NH$_3$)$_2$(Me$_2$Imt)$_2$].2NO$_3$ (3), cis-[Pt(NH$_3$)$_2$(Et$_2$Imt)$_2$].2NO$_3$ (4), cis-[Pt(NH$_3$)$_2$(PrImt)$_2$].2NO$_3$ (5), cis-[Pt(NH$_3$)$_2$(iPrImt)$_2$].2NO$_3$ (6), cis-[Pt(NH$_3$)$_2$(iPr$_2$Imt)$_2$].2NO$_3$ (7), cis-[Pt(NH$_3$)$_2$(Diaz)$_2$].2NO$_3$ (8), cis-[Pt(NH$_3$)$_2$(EtDiaz)$_2$].2NO$_3$ (9), and cis-[Pt(NH$_3$)$_2$(Diap)$_2$].2NO$_3$ (10) wherein Imt is imidazolidine-2-thione, MeImt is N-methylimidazolidine-2-thione, Me$_2$Imt is N,N'-dimethylimidazolidine-2-thione, Et$_2$Imt is N,N'-diethylimidazolidine-2-thione, PrImt is N-propylimidazolidine-2-thione, iPrImt is N-isopropyl)imidazolidine-2-thione, iPr$_2$Imt is N,N'-(di-isopropyl)imidazolidine-2-thione, Diaz is diazinane-2-thione, and Diap is 1,3-Diazepane-2-thione.

7. The method of claim 1, wherein the proliferative disease, disorder or condition is cancer.

8. The method of claim 1, wherein the proliferative disease, disorder or condition is not cancer.

9. The method of claim 1, wherein the proliferative disease, disorder or condition is cancer that is or has become resistant to cisplatin or wherein the complex produces less nephrotoxicity or neurotoxicity than the same dose of cisplatin.

10. The method of claim 1, wherein the proliferative disease, disorder, or condition is breast cancer.

11. The method of claim 1, wherein the proliferative disease, disorder, or condition is colon cancer.

12. The method of claim 1, wherein the proliferative disease, disorder, or condition is lung cancer.

13. A cis-diamine platinum(II) thione complex of the formula [Pt(N R$_1$R$_2$)$_2$(thione)$_2$].2[anion]; wherein R$_1$ and R$_2$ are, independently, hydrogen, alkyl or aryl.

14. The cis-diamine platinum(II) thione complex of claim 12, wherein the thione molecule used to produce the complex is selected from the group consisting of:

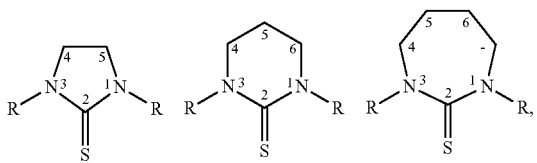

wherein R, independently, is H, alkyl, or aryl.

15. The cis-diamine platinum(II) thione complex of claim 14, wherein the thione molecule used to produce the complex is selected from the group consisting of:

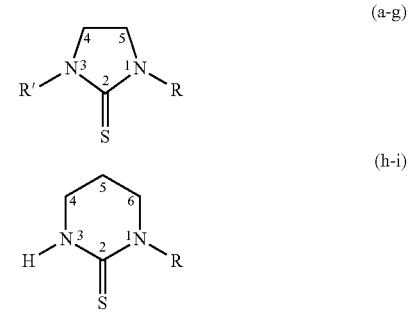

(j)

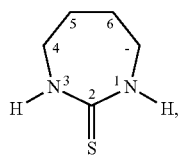

wherein in (a) R=R'=H; (b) R=H, R'=CH₃; (c) R=CH₃, R'=CH₃; (d) R=R'=C₂H₅; (e) R=H, R'=C₃H₇; (f) R=H, R'=i-C₃H₇; (g) R=R'=i-C₃H₇; (h) R=H; (i) R=C₂H₅; and (j) is 1,3-Diazepane-2-thione (Diap).

16. The cis-diamine platinum(II) thione complex of claim 14, wherein the platinum (II) complex has the formula Pt(NH₃)₂(Thione)₂].2NO₃ or a variant complex wherein one or two of the NO₃ anions are replaced with one or more different anions.

17. The cis-diamine platinum(II) thione complex of claim 14, wherein the complex is selected from the group consisting of at least one of cis-[Pt(NH₃)₂(Imt)₂].2NO₃ (1), cis-[Pt(NH₃)₂(MeImt)₂].2NO₃ (2), cis-[Pt(NH₃)₂(Me₂Imt)₂].2NO₃ (3), cis-[Pt(NH₃)₂(Et₂Imt)₂].2NO₃ (4), cis-[Pt(NH₃)₂(PrImt)₂].2NO₃ (5), cis-[Pt(NH₃)₂(iPrImt)₂].2NO₃ (6), cis-[Pt(NH₃)₂(iPr₂Imt)₂].2NO₃ (7), cis-[Pt(NH₃)₂(Diaz)₂].2NO₃ (8), cis-[Pt(NH₃)₂(EtDiaz)₂].2NO₃ (9), and cis-[Pt(NH₃)₂(Diap)₂].2NO₃ (10), or a variant complex wherein one or two of the NO₃ anions are replaced with one or more different anions: wherein Imt is imidazolidine-2-thione, MeImt is N-methylimidazolidine-2-thione, Me₂Imt is N,N'-dimethylimidazolidine-2-thione, Et₂Imt is N,N'-diethylimidazolidine-2-thione, PrImt is N-propylimidazolidine-2-thione, iPrImt is N-isopropyl)imidazolidine-2-thione, iPr₂Imt is N,N-(di-isopropyl)imidazolidine-2-thione, Diaz is diazinane-2-thione, and Diap is 1,3-Diazepane-2-thione.

18. The cis-diamine platinum(II) thione complex of claim 14, wherein both anions are NO₃.

19. A pharmaceutical composition comprising at least one cis-diamine platinum(II) thione complex of claim 13 in combination with at least one pharmaceutically acceptable carrier or excipient.

20. The pharmaceutical composition of claim 19 that further comprises another anticancer drug, chemotherapeutic agent, or immunopotentiator.

* * * * *